United States Patent
Schwartz et al.

(10) Patent No.: US 12,046,326 B2
(45) Date of Patent: Jul. 23, 2024

(54) METHODS AND SYSTEMS FOR USE IN CANCER PREDICTION

(71) Applicant: Carnegie Mellon University, Pittsburgh, PA (US)

(72) Inventors: Russell Schwartz, Pittsburgh, PA (US); Jian Ma, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 771 days.

(21) Appl. No.: 16/854,378

(22) Filed: Apr. 21, 2020

(65) Prior Publication Data

US 2020/0342956 A1    Oct. 29, 2020

Related U.S. Application Data

(60) Provisional application No. 62/838,649, filed on Apr. 25, 2019.

(51) Int. Cl.
*G16B 20/20*    (2019.01)
*G16B 10/00*    (2019.01)
*G16B 30/00*    (2019.01)
*G16B 40/00*    (2019.01)

(52) U.S. Cl.
CPC .............. *G16B 20/20* (2019.02); *G16B 10/00* (2019.02); *G16B 30/00* (2019.02); *G16B 40/00* (2019.02)

(58) Field of Classification Search
USPC .......................................................... 702/19
See application file for complete search history.

(56) References Cited

U.S. PATENT DOCUMENTS

2017/0298441 A1* 10/2017 Wu ...................... C12Q 1/6858

OTHER PUBLICATIONS

Suchorska, Bogdana, et al. "Contrast enhancement is a prognostic factor in IDH1/2 mutant, but not in wild-type WHO grade II/III glioma as confirmed by machine learning." European Journal of Cancer 107 (2019): 15-27. (Year: 2019).*

El-Kebir, Mohammed, et al. "Reconstruction of clonal trees and tumor composition from multi-sample sequencing data." Bioinformatics 31.12 (2015): i62-i70. (Year: 2015).*
Kothen-Hill, Steven T., et al. "Deep learning mutation prediction enables early stage lung cancer detection in liquid biopsy." (2018). (Year: 2018).*
Zairis, Sakellarios. Quantitative Approaches to the Genomics of Clonal Evolution. Columbia University, 2018. (Year: 2018).*
"K-nearest neighbors algorithm." Wikipedia, the Free Encyclopedia. Wikipedia, the Free Encyclopedia, Sep. 5, 2023. Web. Sep. 18, 2023. (Year: 2023).*
Eaton et al., "Deconvolution and phylogeny inference of structural variations in tumor genomic samples", Bioinformatics, 2018, vol. 34, pp. i357-i365.
Jiang et al., "Assessing intratumor heterogeneity and tracking longitudinal and spatial clonal evolutionary history by next-generation sequencing", Proceedings of the National Academy of Sciences of the United States of America, 2016, vol. 113, pp. E5528-E5537.
Li et al., "Allele-Specific Quantification of Structural Variations in Cancer Genomes", Cell Systems, 2016, vol. 3:1, pp. 21-34.
Nielsen et al., "Genotype and SNP calling from next-generation sequencing data", Nature Reviews Genetics, 2011, vol. 12:6, pp. 443-451.
Ritchie et al., "Computational approaches to interpreting genomic sequence variation", Genome Medicine, 2014, vol. 6:87, 11 pages.
"Variant Calling at the GDC", National Cancer Institute Genomic Data Commons, available at gdc.cancer.gov/about-gdc/variant-calling-gdc.
Wang et al., "Machine Learning for Survival Analysis: A Survey", ACM Computing Surveys, 2017, 39 pages.

* cited by examiner

*Primary Examiner* — G. Steven Vanni
(74) *Attorney, Agent, or Firm* — The Webb Law Firm

(57) ABSTRACT

Provided herein are systems, methods, and computer program products using tumor phylogeny, mutation rates, and machine learning to produce a clinical projection, such as patient survival, risk of malignancy, and therapeutic options. The method includes generating sequence variation data that identifies, characterizes, or quantifies at least one mutation in tumor sequence data of a tumor of a patient. The method also includes generating a phylogenic tree depicting clonal evolution of cells in the tumor of the patient. The method further includes determining at least one feature of the phylogenic tree including at least one value quantifying rates of mutation and/or at least one value representing at least one aspect of a structure of the phylogenic tree. The method further includes training a machine learning model to be configured to generate a projection for the patient comprising a clinical outcome or disease progression.

20 Claims, 6 Drawing Sheets

METHODS AND SYSTEMS FOR USE IN CANCER PREDICTION

CROSS REFERENCE TO RELATED APPLICATIONS

This application claims the benefit of U.S. Provisional Patent Application No. 62/838,649, filed Apr. 25, 2019, which is incorporated herein by reference in its entirety.

BACKGROUND

Provided herein are systems and methods for use in cancer prediction.

Cancers are caused by accumulation of somatic alterations, leading to a phenotype of uncontrolled cell growth. In most cases, this accumulation is a product of somatic hypermutability, in which defects in the DNA replication mechanism cause rapid acquisition of mutations across generations of cell growth. The resulting genetic diversification causes a rapid accumulation of mutations, most selectively neutral but some with phenotypic effects, resulting in profound intratumor heterogeneity (ITH), i.e., cell-to-cell variation in the genome. That heterogeneity in turn creates an opportunity for selection for mutations that promote uncontrolled cell growth, leading ultimately to the phenotype of tumor growth and potentially subsequent tumor progression, metastasis, and patient mortality. This process of evolutionary diversification and selection similarly underlies the development of cancer resistance to therapeutic interventions. Understanding this process of somatic evolution is thus crucial to the hard problem of understanding why some precancerous lesions progress to cancer while others do not, why some cancers are highly aggressive and others indolent, and some respond robustly to treatment and others do not.

One of the key insights into cancer progression in the genomic era is that mechanisms of somatic evolution can differ widely across cancer types, between distinct patients for a single cancer type, and even between distinct cell lineages in a single tumor. Some cancers are prone to point mutation hypermutability, others to microsatellite instability, and others to chromosome instability. Even within these broad classes, there are now numerous recognized "mutator phenotypes" presumed to be caused by distinct hypermutability mutations. For example, approximately thirty known point mutation signatures are known to act differentially in different cancers, with several either known to be connected to specific kinds of hypermutability defects (e.g., pol-ε defect, apolipoprotein B mRNA-editing catalytic polypeptide-like (APOBEC) defect, or various DNA mismatch repair defects such as are induced by germline BRCA1 or BRCA2 (Breast Cancer 1 or Breast Cancer 2) mutations), as well as distinct signatures of structural variation mutation, such as is characteristic of chromosome instability due to TP53 (Tumor Protein 53, or p53) function. At present, a number of these signatures of hypermutability remain of unknown origin and it remains to be seen which others might be detected as we gain better power to resolve broader classes of mutations and precisely quantify them via deep sequencing.

SUMMARY

According to non-limiting embodiments or aspects, provided is a system including at least one processor and a non-transitory computer-readable medium storing program instructions. The program instructions are configured to cause the at least one processor to generate sequence variation data that identifies, characterizes, or quantifies at least one mutation in tumor sequence data of a tumor of a patient as compared to normal sequence data obtained from normal cells of the patient or as compared to reference sequence data, wherein the at least one mutation includes at least one of the following: at least one single nucleotide variation, at least one copy-number alteration, at least one structural variation, or any combination thereof. The program instructions are configured to cause the at least one processor to generate, using the sequence variation data, one or more phylogenic trees depicting clonal evolution of cells in the tumor of the patient, each phylogenic tree including a plurality of nodes representing tumor cell clones and edges describing inferred evolutionary relationships between the plurality of nodes. The program instructions are configured to cause the at least one processor to determine at least one feature of the one or more phylogenic trees, the at least one feature including at least one value quantifying rates of mutation and/or at least one value representing at least one aspect of a structure of the one or more phylogenic trees. The program instructions are configured to cause the at least one processor to train a machine learning model, based on the at least one feature of the one or more phylogenic trees, to be configured to generate a projection for the patient including a clinical outcome or disease progression.

According to non-limiting embodiments or aspects, provided is a system including at least one processor and a non-transitory computer-readable medium storing program instructions. The program instructions are configured to cause the at least one processor to generate sequence variation data that identifies, characterizes, or quantifies at least one sequence variation in tumor sequence data of a tumor of each patient of a group of patients as compared to either normal sequence data obtained from normal cells of the group of patients or to reference sequence data, wherein the at least one sequence variation includes at least one of the following: at least one single nucleotide variation, at least one copy-number alteration, at least one structural variation, or any combination thereof. The program instructions are configured to cause the at least one processor to generate, for each patient of the group of patients, using the sequence variation data, one or more phylogenic trees depicting clonal evolution of cells in the tumor of the patient, each phylogenic tree including a plurality of nodes representing tumor cell clones and edges describing inferred evolutionary relationships between the plurality of nodes. The program instructions are configured to cause the at least one processor to determine, for each patient of the group of patients, at least one feature of the one or more phylogenic trees of the patient, the at least one feature including at least one value quantifying rates of mutation and/or at least one value representing at least one aspect of a structure of the one or more phylogenic trees of the patient. The program instructions are configured to cause the at least one processor to train a machine learning model, based on the at least one feature of the one or more phylogenic trees for each patient of the group of patients, to be configured to generate a classification or stratification of the group of patients into two or more cohorts, the two or more cohorts representing a projection of clinical outcome or disease progression for the group of patients.

In further non-limiting embodiments or aspects, the tumor sequence data may include a whole genome sequence or a whole exome sequence of cells of the tumor of the patient. The normal sequence data may be obtained from normal cells or other source of normal genetic material of the patient and is whole genome sequence data.

In further non-limiting embodiments or aspects, the machine learning model may be further trained using at least one clinical feature and/or at least one driver feature.

The machine learning model may include a classification or regression algorithm. The machine learning model may include a Cox regression algorithm, a support vector machine algorithm, or a random forest algorithm. The at least one feature of the one or more phylogenic trees, the at least one clinical feature, and the at least one driver feature used for the machine learning model may be optimized in a computer-implemented step-wise feature selection algorithm for maximizing a concordance index of predictions.

In further non-limiting embodiments or aspects, the sequence variation data may include a value representing at least one of the following: an overall number of nucleic acid sequence substitutions in the tumor sequence data as compared to the normal sequence data or the reference sequence data; a number of specific nucleic acid sequence substitutions, including one or more of the following specific nucleic acid sequence substitutions: A→T, A→C, A→G, T→A, T→C, T→G, C→A, C→T, C→G, G→A, G→T, or G→C, in the tumor sequence data as compared to the normal sequence data or the reference sequence data; a number of gene mutations in the tumor sequence data; a number of clones in the one or more phylogenic trees; a number of single-nucleotide variations, copy-number alterations, and/or structural variations in a largest clone and/or a smallest clone of the one or more phylogenic trees; a mean, maximum, minimum, and/or variance in a number of mutations along a path between two leaf nodes of the one or more phylogenic trees; a number of mutations required from a root node to a leaf node of the one or more phylogenic trees; a maximum number of single-nucleotide variations, copy-number alterations, and/or structural variations in a clone of the one or more phylogenic trees; a total number of single-nucleotide variations, copy-number alterations, and/or structural variations in the one or more phylogenic trees; and a number of copy-number alterations over and/or below a value ranging from 100,000 to 1,000,000 nucleotides in length.

In further non-limiting embodiments or aspects, the machine learning model may be a classification model configured to produce a measure of patient survival or a measure of cancer metastasis as an output representing the projection for the patient including the clinical outcome.

In further non-limiting embodiments or aspects, the machine learning model may be a classification model configured to produce a value indicating survival of a patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as an output representing the projection for the patient including the clinical outcome.

In further non-limiting embodiments or aspects, the at least one feature of the one or more phylogenic trees may include a value quantifying single nucleotide variations, copy-number alterations, and/or structural variations. The machine learning model may include a regression model trained to produce a patient survival curve as an output representing the projection for the patient including the clinical outcome.

According to non-limiting embodiments or aspects, provided is a computer-implemented method. The method includes receiving or preparing, with at least one processor, a sequence data file including tumor sequence data of cells of a tumor of a patient. The method includes generating, with the at least one processor, sequence variation data that identifies, characterizes, or quantifies at least one mutation in the tumor sequence data as compared to normal sequence data obtained from normal cells of the patient or as compared to reference sequence data, wherein the at least one mutation includes at least one of the following: at least one single nucleotide variation, at least one copy-number alterations, at least one structural variation, or any combination thereof. The method includes generating, with the at least one processor, using the sequence variation data, one or more phylogenic trees depicting clonal evolution of cells in the tumor of the patient, each phylogenic tree including a plurality of nodes representing tumor cell clones and edges describing inferred evolutionary relationships between the plurality of nodes. The method includes determining, with the at least one processor, at least one feature of the one or more phylogenic trees associated with one or more nodes of the one or more phylogenic trees, the at least one feature including at least one value quantifying rates of mutation and/or at least one value representing at least one aspect of a structure of the one or more phylogenic trees. The method includes training, with the at least one processor, based on the at least one feature of the one or more phylogenic trees, a machine learning model to be configured to generate a projection for the patient including a clinical outcome or disease progression for the patient.

In further non-limiting embodiments or aspects, the method may include generating, with the at least one processor, an output representing the projection, the output configured to be used to adapt a treatment process of the patient based on the output.

According to non-limiting embodiments or aspects, provided is a computer-implemented method. The method includes receiving or preparing, with at least one processor, a sequence data file including tumor sequence data of cells of a tumor of each patient of a group of patients. The method includes generating, with the at least one processor, sequence variation data that identifies, characterizes, or quantifies at least one mutation in the tumor sequence data of each patient of the group of patients as compared to normal sequence data obtained from normal cells of the group of patients or as compared to reference sequence data, wherein the at least one mutation includes at least one of the following: at least one single nucleotide variation, at least one copy-number alteration, at least one structural variation, or any combination thereof. The method includes generating, with the at least one processor, for each patient of the group of patients, using the sequence variation data, one or more phylogenic trees depicting clonal evolution of cells in the tumor of the patient, each phylogenic tree including a plurality of nodes representing tumor cell clones and edges describing inferred evolutionary relationships between the plurality of nodes. The method includes determining, with the at least one processor, for each patient of the group of patients, at least one feature of the one or more phylogenic trees associated with one or more nodes of the one or more phylogenic trees, the at least one feature including at least one value quantifying rates of mutation and/or at least one value representing at least one aspect of a structure of the one or more phylogenic trees. The method includes training, with the at least one processor, based on the at least one feature of the one or more phylogenic trees for each patient of the group of patients, a machine learning model to be configured to generate a classification or stratification of the group of patients into two or more cohorts, the two or more cohorts representing a projection of clinical outcome or disease progression for the group of patients. The method includes generating, with the at least one processor, an output representing the projection, the output configured to be used to classify the group of patients in a clinical trial into the two or more cohorts.

In further non-limiting embodiments or aspects, the method may include sequencing DNA obtained from at least one biopsy of the tumor of the patient or other source of tumor genetic material in the patient to generate the sequence data file including tumor sequence data of nucleic acid obtained from the at least one biopsy or the other source of tumor genetic material.

In further non-limiting embodiments or aspects, the tumor sequence data may include a whole genome sequence or a whole exome sequence of the cells of the tumor. The normal sequence data may be obtained from normal cells or other source of normal genetic material of the patient, and the normal sequence data may be whole genome sequence data. The method may include sequencing DNA obtained from the normal cells or the other source of normal genetic material of the patient to generate the normal sequence data.

In further non-limiting embodiments or aspects, the machine learning model may be further trained using at least one clinical feature and/or at least one driver feature. The machine learning model may include a classification or regression algorithm. The machine learning model may include a Cox regression algorithm, a support vector machine algorithm, or a random forest algorithm. The at least one feature of the one or more phylogenic trees, the at least one clinical feature, and the at least one driver feature used for the machine learning model may be optimized in a computer-implemented step-wise feature selection algorithm for maximizing a concordance index of predictions.

In further non-limiting embodiments or aspects, the sequence variation data may include a value representing one or more of the following: an overall number of nucleic acid sequence substitutions in the tumor sequence data as compared to the normal sequence data or the reference sequence data; a number of specific nucleic acid sequence substitutions, including at least one of the following specific nucleic acid sequence substitutions: A→T, A→C, A→G, T→A, T→C, T→G, C→A, C→T, C→G, G→A, G→T, or G→C in the tumor sequence data as compared to the normal sequence data or the reference sequence data; a number of gene mutations in the tumor sequence data; a number of clones in the one or more phylogenic trees; a number of single-nucleotide variations, copy-number alterations, and/or structural variations in a largest clone and/or a smallest clone of the one or more phylogenic trees; a mean, maximum, minimum, and/or variance in a number of mutations along a path between two leaf nodes of the one or more phylogenic trees; a number of mutations required from a root node to a leaf node of the one or more phylogenic trees; a maximum number of single-nucleotide variations, copy-number alterations, and/or structural variations in a clone of the one or more phylogenic trees; a total number of single-nucleotide variations, copy-number alterations, and/or structural variations in the one or more phylogenic trees; a number of copy-number alterations over and/or below a value ranging from 100,000 to 1,000,000 nucleotides in length.

In further non-limiting embodiments or aspects, the machine learning model may be a classification model trained to produce a measure of patient survival or a measure of cancer metastasis as the output representing the projection of the clinical outcome for the patient. The machine learning model may be a classification model configured to produce a value indicating survival of a patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as the output representing the projection for the patient including the clinical outcome.

In further non-limiting embodiments or aspects, the at least one feature of the one or more phylogenic trees may be a value quantifying a rate of single nucleotide variations, copy-number alterations, and/or structural variations. The machine learning model may be a regression model trained to produce a patient survival curve as the output representing the projection of the clinical outcome for the patient.

According to non-limiting embodiments or aspects, provided is a non-transitory computer storage medium storing program instructions. The program instructions are configured to cause at least one processor to generate sequence variation data that identifies, characterizes, or quantifies at least one mutation in tumor sequence data of a tumor of a patient as compared to normal sequence data obtained from normal cells of the patient or as compared to reference sequence data, wherein the at least one mutation includes at least one of the following: at least one single nucleotide variation, at least one copy-number alteration, at least one structural variation, or any combination thereof. The program instructions are configured to cause at least one processor to generate, using the sequence variation data, one or more phylogenic trees depicting clonal evolution of cells in the tumor of the patient, each phylogenic tree including a plurality of nodes representing tumor cell clones and edges describing inferred evolutionary relationships between the plurality of nodes. The program instructions are configured to cause at least one processor to determine at least one feature of the one or more phylogenic trees, the at least one feature including at least one value quantifying rates of mutation and/or at least one value representing at least one aspect of a structure of the one or more phylogenic trees. The program instructions are configured to cause at least one processor to train a machine learning model, based on the at least one feature of the one or more phylogenic trees, to be configured to generate a projection for the patient including a clinical outcome or disease progression.

According to non-limiting embodiments or aspects, provided is a computer storage medium storing program instructions. The program instructions are configured to cause at least one processor to generate sequence variation data that identifies, characterizes, or quantifies at least one sequence variation in tumor sequence data of a tumor of each patient of a group of patients as compared to either normal sequence data obtained from normal cells of the group of patients or to reference sequence data, wherein the at least one sequence variation includes at least one of the following: at least one single nucleotide variation, at least one copy-number alteration, at least one structural variation, or any combination thereof. The program instructions are configured to cause at least one processor to generate, for each patient of the group of patients, using the sequence variation data, one or more phylogenic trees depicting clonal evolution of cells in the tumor of the patient, each phylogenic tree including a plurality of nodes representing tumor cell clones and edges describing inferred evolutionary relationships between the plurality of nodes. The program instructions are configured to cause at least one processor to determine, for each patient of the group of patients, at least one feature of the one or more phylogenic trees of the patient, the at least one feature including at least one value quantifying rates of mutation and/or at least one value representing at least one aspect of a structure of the one or more phylogenic trees of the patient. The program instructions are configured to cause at least one processor to train a machine learning model, based on the at least one feature of the one or more phylogenic trees for each patient of the group of patients, to be configured to generate a classification or stratification of the group of patients into two or more cohorts, the two or more cohorts representing a projection of clinical outcome or disease progression for the group of patients.

In further non-limiting embodiments or aspects, the tumor sequence data may include a whole genome sequence or a whole exome sequence of cells of a tumor of the patient. The normal sequence data may be obtained from normal cells of the patient and includes whole genome sequence data.

In further non-limiting embodiments or aspects, the machine learning model may be further trained using at least one clinical feature and/or at least one driver feature. The machine learning model may include a classification or regression algorithm. The machine learning model may include a Cox regression algorithm, a support vector machine algorithm, or a random forest algorithm. The at least one feature of the one or more phylogenic trees, the at least one clinical feature, and the at least one driver feature used for the machine learning model may be optimized in a computer-implemented step-wise feature selection algorithm for maximizing a concordance index of predictions.

In further non-limiting embodiments or aspects, the sequence variation data may include a value representing one or more of the following: an overall number of nucleic acid sequence substitutions in the tumor sequence data as compared to the normal sequence data or the reference sequence data; a number of specific nucleic acid sequence substitutions, including at least one of the following specific nucleic acid sequence substitutions: A→T, A→C, A→G, T→A, T→C, T→G, C→A, C→T, C→G, G→A, G→T, or G→C in the tumor sequence data as compared to the normal sequence data or the reference sequence data; a number of gene mutations in the tumor sequence data; a number of clones in the one or more phylogenic trees; a number of single-nucleotide variations, copy-number alterations, and/or structural variations in a largest clone and/or a smallest clone of the one or more phylogenic trees; a mean, maximum, minimum, and/or variance in a number of mutations along a path between two leaf nodes of the one or more phylogenic trees; a number of mutations required from a root node to a leaf node of the one or more phylogenic trees; a maximum number of single-nucleotide variations, copy-number alterations, and/or structural variations in a clone of the one or more phylogenic trees; a total number of single-nucleotide variations, copy-number alterations, and/or structural variations in the one or more phylogenic trees; a number of copy-number alterations over and/or below a value ranging from 100,000 to 1,000,000 nucleotides in length.

In further non-limiting embodiments or aspects, the machine learning model may be a classification model trained to produce a measure of patient survival or a measure of cancer metastasis as an output representing the projection of the clinical outcome for the patient.

In further non-limiting embodiments or aspects, the machine learning model may be a classification model trained to produce a value indicating survival of a patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as the output representing the projection for the patient including the clinical outcome.

In further non-limiting embodiments or aspects, the at least one feature of the one or more phylogenic trees may be a value quantifying single nucleotide variations, copy-number alterations, and/or structural variations. The machine learning model may include a regression model trained to produce a patient survival curve as an output representing the projection of the clinical outcome for the patient.

Other non-limiting embodiments or aspects of the present disclosure will be set forth in the following numbered clauses:

Clause 1: A system comprising at least one processor and a non-transitory computer-readable medium storing program instructions configured to cause the at least one processor to: generate sequence variation data that identifies, characterizes, or quantifies at least one mutation in tumor sequence data of a tumor of a patient as compared to normal sequence data obtained from normal cells of the patient or as compared to reference sequence data, wherein the at least one mutation comprises at least one of the following: at least one single nucleotide variation, at least one copy-number alteration, at least one structural variation, or any combination thereof; generate, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes; determine at least one feature of the one or more phylogenic trees, the at least one feature comprising at least one value quantifying rates of mutation and/or at least one value representing at least one aspect of a structure of the one or more phylogenic trees; and train a machine learning model, based on the at least one feature of the one or more phylogenic trees, to be configured to generate a projection for the patient comprising a clinical outcome or disease progression.

Clause 2: A system comprising at least one processor and a non-transitory computer-readable medium storing program instructions configured to cause the at least one processor to: generate sequence variation data that identifies, characterizes, or quantifies at least one sequence variation in tumor sequence data of a tumor of each patient of a group of patients as compared to either normal sequence data obtained from normal cells of the group of patients or to reference sequence data, wherein the at least one sequence variation comprises at least one of the following: at least one single nucleotide variation, at least one copy-number alteration, at least one structural variation, or any combination thereof; generate, for each patient of the group of patients, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes; determine, for each patient of the group of patients, at least one feature of the one or more phylogenic trees of the patient, the at least one feature comprising at least one value quantifying rates of mutation and/or at least one value representing at least one aspect of a structure of the one or more phylogenic trees of the patient; and train a machine learning model, based on the at least one feature of the one or more phylogenic trees for each patient of the group of patients, to be configured to generate a classification or stratification of the group of patients into two or more cohorts, the two or more cohorts representing a projection of clinical outcome or disease progression for the group of patients.

Clause 3: The system of clause 1 or 2, wherein the tumor sequence data comprises a whole genome sequence or a whole exome sequence of cells of the tumor of the patient.

Clause 4: The system of any of clauses 1-3, wherein the normal sequence data is obtained from normal cells or other source of normal genetic material of the patient and is whole genome sequence data.

Clause 5: The system of any of clauses 1-4, wherein the machine learning model is further trained using at least one clinical feature and/or at least one driver feature.

Clause 6: The system of any of clauses 1-5, wherein the machine learning model comprises a classification or regression algorithm.

Clause 7: The system of any of clauses 1-6, wherein the machine learning model comprises a Cox regression algorithm, a support vector machine algorithm, or a random forest algorithm.

Clause 8: The system of any of clauses 1-7, wherein the at least one feature of the one or more phylogenic trees, the at least one clinical feature, and the at least one driver feature used for the machine learning model are optimized in a computer-implemented step-wise feature selection algorithm for maximizing a concordance index of predictions.

Clause 9: The system of any of clauses 1-8, wherein the sequence variation data includes a value representing at least one of the following: an overall number of nucleic acid sequence substitutions in the tumor sequence data as compared to the normal sequence data or the reference sequence data; a number of specific nucleic acid sequence substitutions, including one or more of the following specific nucleic acid sequence substitutions: A→T, A→C, A→G, T→A, T→C, T→G, C→A, C→T, C→G, G→A, G→T, or G→C, in the tumor sequence data as compared to the normal sequence data or the reference sequence data; a number of gene mutations in the tumor sequence data; a number of clones in the one or more phylogenic trees; a number of single-nucleotide variations, copy-number alterations, and/or structural variations in a largest clone and/or a smallest clone of the one or more phylogenic trees; a mean, maximum, minimum, and/or variance in a number of mutations along a path between two leaf nodes of the one or more phylogenic trees; a number of mutations required from a root node to a leaf node of the one or more phylogenic trees; a maximum number of single-nucleotide variations, copy-number alterations, and/or structural variations in a clone of the one or more phylogenic trees; a total number of single-nucleotide variations, copy-number alterations, and/or structural variations in the one or more phylogenic trees; and a number of copy-number alterations over and/or below a value ranging from 100,000 to 1,000,000 nucleotides in length.

Clause 10: The system of any of clauses 1-9, wherein the machine learning model is a classification model configured to produce a measure of patient survival or a measure of cancer metastasis as an output representing the projection for the patient comprising the clinical outcome.

Clause 11: The system of any of clauses 1-10, wherein the machine learning model is a classification model configured to produce a value indicating survival of a patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as an output representing the projection for the patient comprising the clinical outcome.

Clause 12: The system of any of clauses 1-11, wherein the at least one feature of the one or more phylogenic trees comprises a value quantifying single nucleotide variations, copy-number alterations, and/or structural variations.

Clause 13: The system of any of clauses 1-12, wherein the machine learning model comprises a regression model trained to produce a patient survival curve as an output representing the projection for the patient comprising the clinical outcome.

Clause 14: A computer-implemented method comprising: receiving or preparing, with at least one processor, a sequence data file comprising tumor sequence data of cells of a tumor of a patient; generating, with the at least one processor, sequence variation data that identifies, characterizes, or quantifies at least one mutation in the tumor sequence data as compared to normal sequence data obtained from normal cells of the patient or as compared to reference sequence data, wherein the at least one mutation comprises at least one of the following: at least one single nucleotide variation, at least one copy-number alterations, at least one structural variation, or any combination thereof; generating, with the at least one processor, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes; determining, with the at least one processor, at least one feature of the one or more phylogenic trees associated with one or more nodes of the one or more phylogenic trees, the at least one feature comprising at least one value quantifying rates of mutation and/or at least one value representing at least one aspect of a structure of the one or more phylogenic trees; and training, with the at least one processor, based on the at least one feature of the one or more phylogenic trees, a machine learning model to be configured to generate a projection for the patient comprising a clinical outcome or disease progression for the patient.

Clause 15: The computer-implemented method of clause 14, further comprising generating, with the at least one processor, an output representing the projection, the output configured to be used to adapt a treatment process of the patient based on the output.

Clause 16: A computer-implemented method comprising: receiving or preparing, with at least one processor, a sequence data file comprising tumor sequence data of cells of a tumor of each patient of a group of patients; generating, with the at least one processor, sequence variation data that identifies, characterizes, or quantifies at least one mutation in the tumor sequence data of each patient of the group of patients as compared to normal sequence data obtained from normal cells of the group of patients or as compared to reference sequence data, wherein the at least one mutation comprises at least one of the following: at least one single nucleotide variation, at least one copy-number alteration, at least one structural variation, or any combination thereof;

generating, with the at least one processor, for each patient of the group of patients, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes; determining, with the at least one processor, for each patient of the group of patients, at least one feature of the one or more phylogenic trees associated with one or more nodes of the one or more phylogenic trees, the at least one feature comprising at least one value quantifying rates of mutation and/or at least one value representing at least one aspect of a structure of the one or more phylogenic trees; training, with the at least one processor, based on the at least one feature of the one or more phylogenic trees for each patient of the group of patients, a machine learning model to be configured to generate a classification or stratification of the group of patients into two or more cohorts, the two or more cohorts representing a projection of clinical outcome or disease progression for the group of patients; and generating, with the at least one processor, an output representing the projection, the output configured to be used to classify the group of patients in a clinical trial into the two or more cohorts.

Clause 17: The computer-implemented method of any of clauses 14-16, further comprising: sequencing DNA obtained from at least one biopsy of the tumor of the patient or other source of tumor genetic material in the patient to generate the sequence data file comprising tumor sequence data of nucleic acid obtained from the at least one biopsy or the other source of tumor genetic material.

Clause 18: The computer-implemented method of any of clauses 14-17, wherein the tumor sequence data comprises a whole genome sequence or a whole exome sequence of the cells of the tumor.

Clause 19: The computer-implemented method of any of clauses 14-18, wherein the normal sequence data is obtained from normal cells or other source of normal genetic material of the patient, and wherein the normal sequence data is whole genome sequence data.

Clause 20: The computer-implemented method of any of clauses 14-19, further comprising: sequencing DNA obtained from the normal cells or the other source of normal genetic material of the patient to generate the normal sequence data.

Clause 21: The computer-implemented method of any of clauses 14-20, wherein the machine learning model is further trained using at least one clinical feature and/or at least one driver feature.

Clause 22: The computer-implemented method of any of clauses 14-21, wherein the machine learning model comprises a classification or regression algorithm.

Clause 23: The computer-implemented method of any of clauses 14-22, wherein the machine learning model comprises a Cox regression algorithm, a support vector machine algorithm, or a random forest algorithm.

Clause 24: The computer-implemented method of any of clauses 14-21, wherein the at least one feature of the one or more phylogenic trees, the at least one clinical feature, and the at least one driver feature used for the machine learning model are optimized in a computer-implemented step-wise feature selection algorithm for maximizing a concordance index of predictions.

Clause 25: The computer-implemented method of any of clauses 14-24, wherein the sequence variation data includes a value representing one or more of the following: an overall number of nucleic acid sequence substitutions in the tumor sequence data as compared to the normal sequence data or the reference sequence data; a number of specific nucleic acid sequence substitutions, including at least one of the following specific nucleic acid sequence substitutions: A→T, A→C, A→G, T→A, T→C, T→G, C→A, C→T, C→G, G→A, G→T, or G→C in the tumor sequence data as compared to the normal sequence data or the reference sequence data; a number of gene mutations in the tumor sequence data; a number of clones in the one or more phylogenic trees; a number of single-nucleotide variations, copy-number alterations, and/or structural variations in a largest clone and/or a smallest clone of the one or more phylogenic trees; a mean, maximum, minimum, and/or variance in a number of mutations along a path between two leaf nodes of the one or more phylogenic trees; a number of mutations required from a root node to a leaf node of the one or more phylogenic trees; a maximum number of single-nucleotide variations, copy-number alterations, and/or structural variations in a clone of the one or more phylogenic trees; a total number of single-nucleotide variations, copy-number alterations, and/or structural variations in the one or more phylogenic trees; a number of copy-number alterations over and/or below a value ranging from 100,000 to 1,000,000 nucleotides in length.

Clause 26: The computer-implemented method of any of clauses 14-25, wherein the machine learning model is a classification model trained to produce a measure of patient survival or a measure of cancer metastasis as the output representing the projection of the clinical outcome for the patient.

Clause 27: The computer-implemented method of any of clauses 14-26, wherein the machine learning model is a classification model configured to produce a value indicating survival of a patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as the output representing the projection for the patient comprising the clinical outcome.

Clause 28: The computer-implemented method of any of clauses 14-27, wherein the at least one feature of the one or more phylogenic trees is a value quantifying a rate of single nucleotide variations, copy-number alterations, and/or structural variations.

Clause 29: The computer-implemented method of any of clauses 14-28, wherein the machine learning model is a regression model trained to produce a patient survival curve as the output representing the projection of the clinical outcome for the patient.

Clause 30: A non-transitory computer storage medium storing program instructions configured to cause at least one processor to: generate sequence variation data that identifies, characterizes, or quantifies at least one mutation in tumor sequence data of a tumor of a patient as compared to normal sequence data obtained from normal cells of the patient or as compared to reference sequence data, wherein the at least one mutation comprises at least one of the following: at least one single nucleotide variation, at least one copy-number alteration, at least one structural variation, or any combination thereof; generate, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes; determine at least one feature of the one or more phylogenic trees, the at least one feature comprising at least one value quantifying rates of mutation and/or at least one value representing at least one aspect of a structure of the one or more phylogenic trees; and train a machine learning model, based on the at least one feature of the one or more phylogenic trees, to be configured to generate a projection for the patient comprising a clinical outcome or disease progression.

Clause 31: A non-transitory computer storage medium storing program instructions configured to cause at least one processor to: generate sequence variation data that identifies, characterizes, or quantifies at least one sequence variation in tumor sequence data of a tumor of each patient of a group of patients as compared to either normal sequence data obtained from normal cells of the group of patients or to reference sequence data, wherein the at least one sequence variation comprises at least one of the following: at least one single nucleotide variation, at least one copy-number alteration, at least one structural variation, or any combination thereof; generate, for each patient of the group of patients, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes; determine, for each patient of the group of patients, at least one feature of the one or more phylogenic trees of the patient, the at least one feature comprising at least one value quantifying rates of mutation and/or at least one value representing at least one aspect of a structure of the one or more phylogenic trees of the patient; and train a machine learning model, based on the at least one feature of the one or more phylogenic trees for each patient of the group of patients, to be configured to generate a classification or stratification of the group of patients into two or more cohorts, the two or more cohorts representing a projection of clinical outcome or disease progression for the group of patients.

Clause 32: The non-transitory computer storage medium of clause 30 or 31, wherein the tumor sequence data comprises a whole genome sequence or a whole exome sequence of cells of a tumor of the patient.

Clause 33: The non-transitory computer storage medium of any of clauses 30-32, wherein the normal sequence data is obtained from normal cells of the patient and comprises whole genome sequence data.

Clause 34: The non-transitory computer storage medium of any of clauses 30-33, wherein the machine learning model is further trained using at least one clinical feature and/or at least one driver feature.

Clause 35: The non-transitory computer storage medium of any of clauses 30-34, wherein the machine learning model comprises a classification or regression algorithm.

Clause 36: The non-transitory computer storage medium of any of clauses 30-35, wherein the machine learning model comprises a Cox regression algorithm, a support vector machine algorithm, or a random forest algorithm.

Clause 37: The non-transitory computer storage medium of any of clauses 30-36, wherein the at least one feature of the one or more phylogenic trees, the at least one clinical feature, and the at least one driver feature used for the machine learning model are optimized in a computer-implemented step-wise feature selection algorithm for maximizing a concordance index of predictions.

Clause 38: The non-transitory computer storage medium of any of clauses 30-37, wherein the sequence variation data includes a value representing one or more of the following: an overall number of nucleic acid sequence substitutions in the tumor sequence data as compared to the normal sequence data or the reference sequence data; a number of specific nucleic acid sequence substitutions, including at least one of the following specific nucleic acid sequence substitutions: A→T, A→C, A→G, T→A, T→C, T→G, C→A, C→T, C→G, G→A, G→T, or G→C in the tumor sequence data as compared to the normal sequence data or the reference sequence data; a number of gene mutations in the tumor sequence data; a number of clones in the one or more phylogenic trees; a number of single-nucleotide variations, copy-number alterations, and/or structural variations in a largest clone and/or a smallest clone of the one or more phylogenic trees; a mean, maximum, minimum, and/or variance in a number of mutations along a path between two leaf nodes of the one or more phylogenic trees; a number of mutations required from a root node to a leaf node of the one or more phylogenic trees; a maximum number of single-nucleotide variations, copy-number alterations, and/or structural variations in a clone of the one or more phylogenic trees; a total number of single-nucleotide variations, copy-number alterations, and/or structural variations in the one or more phylogenic trees; a number of copy-number alterations over and/or below a value ranging from 100,000 to 1,000,000 nucleotides in length.

Clause 39: The non-transitory computer storage medium of any of clauses 30-38, wherein the machine learning model is a classification model trained to produce a measure of patient survival or a measure of cancer metastasis as an output representing the projection of the clinical outcome for the patient.

Clause 40: The non-transitory computer storage medium of any of clauses 30-39, wherein the machine learning model is a classification model trained to produce a value indicating survival of a patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as the output representing the projection for the patient comprising the clinical outcome.

Clause 41: The non-transitory computer storage medium of any of clauses 30-40, wherein the at least one feature of the one or more phylogenic trees is a value quantifying single nucleotide variations, copy-number alterations, and/or structural variations.

Clause 42: The non-transitory computer storage medium of any of clauses 30-41, wherein the machine learning model comprises a regression model trained to produce a patient survival curve as an output representing the projection of the clinical outcome for the patient.

DETAILED DESCRIPTION

Figure 1:
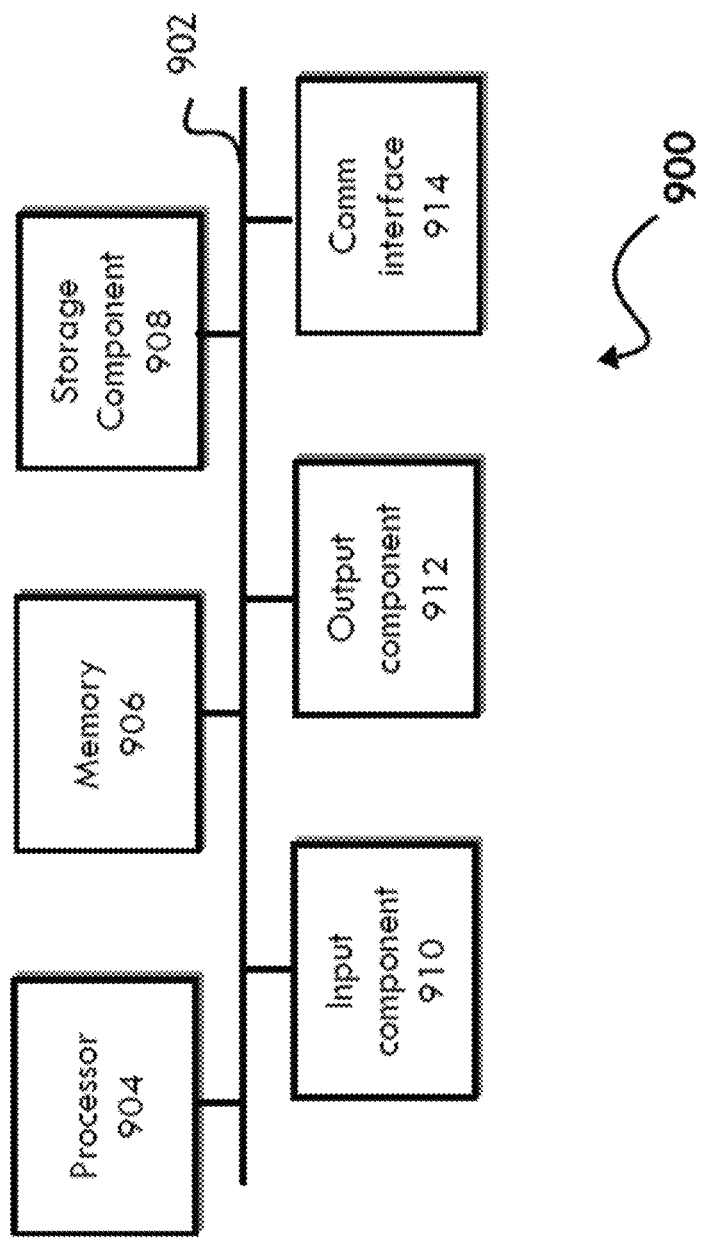
FIG. 1 illustrates example components of a computer device used in connection with non-limiting embodiments.

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects disclosed herein are not to be considered as limiting.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

As used herein, the term "computing device" or "computer" may refer to one or more electronic devices configured to process data. A computing device may, in some examples, include the necessary components to receive, process, and output data, such as a display, a processor, a memory, an input device, and a network interface. A computing device may be a server, a mobile device, a desktop computer, a subsystem or integrated part of a genomic sequencer or sequence analyzer, and/or the like. As an example, a mobile device may include a cellular phone (e.g., a smartphone or standard cellular phone), a portable computer, a wearable device (e.g., watches, glasses, lenses, clothing, and/or the like), a personal digital assistant (PDA), and/or other like devices.

As used herein, "interface" refers, in the context of programming and software modules, to the languages, codes and messages that programs or modules use to communicate with each other and to the hardware, and includes computer code or other data stored on a computer-readable medium that may be executed by a processor to facilitate the interaction between software modules. In some aspects of the methods and systems described herein, software modules, such as the variant calling module, the tumor phylogeny or modules and the machine learning modules are designed as separate software components, modules, or engines, with each requiring specific data input formats, and providing specific data output formats, and, in non-limiting examples, an interface may be used to facilitate such communication between components.

As used herein, the term "graphical user interface" or "GUI" refers to a generated display with which a user may interact, either directly or indirectly (e.g., through a keyboard, mouse, touchscreen, and/or the like).

In addition to providing an improved means of cancer prediction, non-limiting embodiments of the present disclosure provide a technical solution to the shortcomings of predictive modeling. The present systems and methods mitigate the need for a large and periodically sampled dataset of an individual patient's tumor to develop a reliable projection of clinical outcome or disease progression. By training machine learning models to identify and process variations in sequence data, as described below, not only is the accuracy of a computer-generated projection increased, but the resource volume and time in producing a reliable computer-generated projection for a new patient may be decreased. Furthermore, by using the described techniques for groups of patients, patients may be efficiently classified/stratified into cohorts for the purpose of further clinical analysis or trial design, once again reducing time and resources required for individual patient analysis and patient-to-patient comparison.

As shown in FIG. 1, device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 1, storage component 908 may store information and/or software related to the operation and use of device 900. For example, storage component 908 may include a hard disk and/or another type of computer-readable medium (e.g., a magnetic disk, an optical disk, a magneto-optic disk, a solid state disk, cloud storage, etc.). Input component 910 may include a component that permits device 900 to receive information, such as via user input (e.g., a touch screen display, a keyboard, a keypad, a mouse, a button, a switch, a microphone, etc.) or automated input (e.g., from a batch processing script or directly from a sequencing machine or other automated laboratory equipment). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

The computer device can be configured to execute instructions for performing the computer-implemented tasks described herein. Software can be one or more of an operating system (e.g., a Windows™ based operating system), browser application, client application, server application, proxy application, on-line service provider application, and/or private network application. The software, modules, algorithms, interfaces, etc. can be implemented by utilizing any suitable computer language or analytical system (e.g., C\C++, UNIX SHELL SCRIPT, PERL, JAVA™, JAVASCRIPT, HTML/DHTML/XML, FLASH, WINDOWS, UNIX/LINUX, APACHE, RDBMS including ORACLE, INFORMIX, and MySQL, PYTHON, R, LISP, or PROLOG). Commercial software suites for implementation of machine learning, among the other functions and modules described herein, include free, open-source, and proprietary software, such as, without limitation, lifelines, SAS, MATLAB, among many others.

The time needed to obtain whole genome sequences or whole exome sequences and associated costs are both dropping rapidly. Good quality whole genome sequences currently can be obtained for less than $3,000, and whole exome sequences for hundreds of dollars. In the context of cancers, one or two sequencing steps may be conducted. In preparing sequence data for input into a tumor phylogeny algorithm, at least genome sequence data from one or more samples of a patient's tumor or other sources of tumor DNA, such as circulating tumor cells, vesicles, or free DNA, is used. That tumor sequence data is compared to genome sequence data obtained from normal, non-tumor tissue of the patient, or a reference genome sequence. In one aspect, the tumor sequence data is compared to non-tumor sequence data of the patient, because reference sequences that are not the patient's sequences will typically differ from the patient's non-tumor sequences, yielding false variations in sequences. The sequence data can be provided and input into the system described herein in any useful format, such as, without limitation: BAM, CRAM, SAM, or VCF format as are broadly-known in the sequencing arts.

Figure 2:
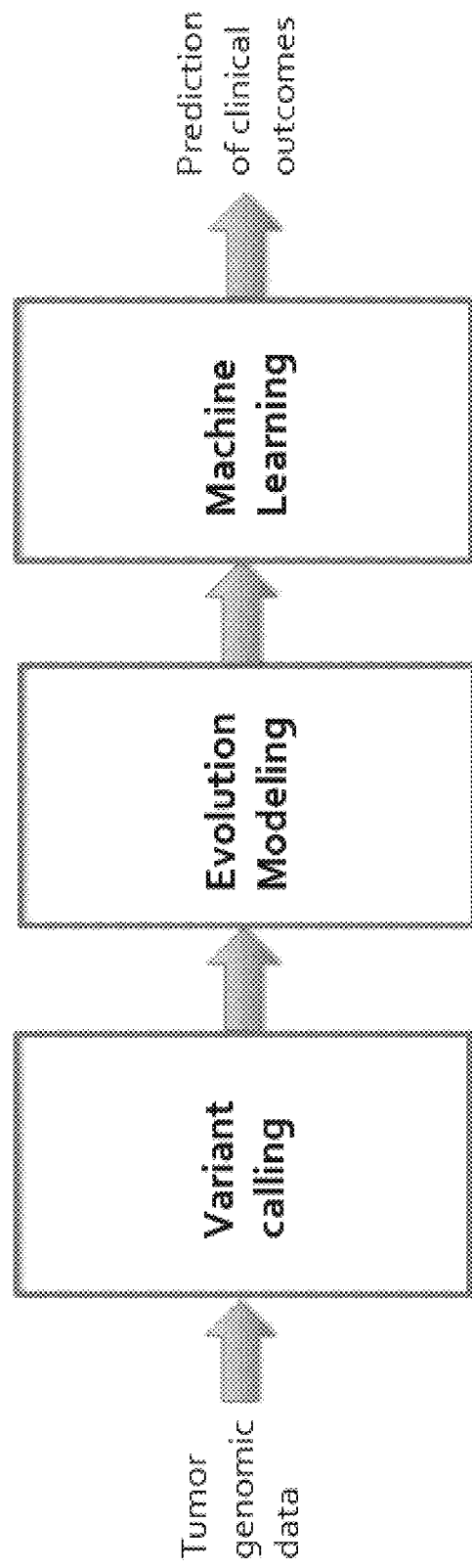
FIG. 2 is a flow diagram outlining process flow for the methods and devices described herein.

Non-limiting embodiments provide for a system and method that leverages nucleic acid sequencing data, e.g., DNA sequencing data such as whole exome sequencing (WES) data or whole genome sequencing (WGS) data, to provide diagnostic tools and treatment options for cancer patients. In non-limiting embodiments, the system receives patient data, or tumor genomic data (FIG. 2). For example, patient data may be inputted through one or more APIs in communication with a computing device configured for executing the programming described herein, or input and output graphical user interfaces (GUIs) accessible through a web browser or other application (e.g., a mobile application on a mobile device).

Referencing FIG. 2, a first module of the system and methods described herein may include a variant calling module, which identifies and produces output identifying, quantifying, or characterizing sequence variations, such as, without limitation, single nucleotide variations, copy-number alterations, structural variations, microsatellite variations, and/or other DNA variations in the tumor sequence data, and driver features, such as polymorphism or copy number information of known or suspected cancer driver genes. Non-DNA variations may also be identified, such as expression changes or epigenetic changes. The evolution modeling step produces a tumor phylogeny tree, which is a representation of clonal evolution of the tumor cells. Features of the tumor phylogeny tree, including features of the structure of the tree and clones/nodes identified in the tumor phylogeny tree, are extracted from the evolutionary modeling step. The machine learning module applies, at least, machine learning classifiers to the features of the tumor phylogeny tree, optionally combined with clinical data and other genomic features, such as driver data, and/or polymorphism data to produce an output relating to survival, metastasis, expected therapy, or adjuvant therapy outcomes or resistance, patient cohort classification, other disease progression outcomes. The machine learning model may optionally include preprocessing and/or feature selection steps to optimize the set of features prior to classification.

In some embodiments, a pool of patients may be classified or stratified, e.g., for risk of metastasis or survival, for example with respect to drug susceptibility or resistance. The pool of patients may be candidates for a clinical trial, or patients who were the subject of a trial. In this way, cohorts can be produced that better represent the efficacy of a trial drug, or past clinical trial data, for example, data from failed clinical trials, may be re-evaluated and better understood. Output may include a classification scheme, for example and without limitation, a stratification of candidates for a clinical trial or of participants in former clinical trials, that separates individuals who are likely to respond to a given treatment and those who are unlikely to respond. By this process, indications can be tailored to specific groups. Failed clinical trials may be evaluated to determine if responders can be separately classified from non-responders.

Variant Calling

The variant calling module both provides the information used to produce a tumor phylogeny tree, and extracts additional features for use in the machine learning step, including driver gene mutation and polymorphism (e.g., SNP) information. For whole genome or exome variant calling, a three step process may be followed: carry out whole genome or whole exome sequencing to create FASTQ files, align the sequences to a reference genome, creating BAM or CRAM files, and identify where the aligned reads differ from the reference genome and write to a VCF file. In germline variant calling, the reference genome is the standard for the species of interest. This allows identification of genotypes. As most non-cancerous genomes are diploid, it is expected that at any given locus, either all reads have the same base, indicating homozygosity, or approximately half of all reads have one base and half have another, indicating heterozygosity. An exception to this would be the sex chromosomes in male mammals. In somatic variant calling, the reference is a related tissue from the same individual. Mosaicism is expected between, e.g., normal cells and tumor cells. A typical variant or mutation calling pipeline may employ software programs, modules, or functions that perform the following broad steps: raw read alignment to a genome reference, such as a WGS obtained from normal tissue of the patient, pre-calling alignment recalibration ("co-cleaning"), raw variant calling, post-call quality assignment, and post-call variant filtering (see, e.g., Nielsen, R., Paul, J., Albrechtsen, A, and Song, Y., Genotype and SNP calling from next-generation sequencing data. Nature Reviews. Genetics 12, 443-451 (2011) and "Variant Calling at the GDC" gdc.cancer.gov/about-gdc/variant-calling-gdc). As indicated below, Weaver is one example of a module that can perform allele-specific SV calls from WGS data.

Additional phylogeny and other evolutionary features include sequence variation data in a tumor, or in cells of a biopsy. Sequence variation data represents the overall rate of mutation in those tumors or cells of a given mutation class or mutation process. Sequence variation data is different from identification of driver genes or driver gene polymorphisms, which may be associated with any given cancer type, and which may be considered during the machine learning module in addition to phylogenic and other evolutionary features. Sequence variation data are one or more quantitative measures of evolutionary rate in a tumor, and includes any useful measure of mutation or mutation rate in aggregate or by subclasses of mutation. Sequence variation data is not specific to any gene or polymorphism, but is a generic measure of mutation rate, for example, A→T, A→G, and T→A are shown in the Examples below to be pertinent to a classification of breast cancer patients. It should be recognized by those of ordinary skill that sequence variations (mutations) may be generated differently in different tumors or tumor classes, and, as such, different quantitative measures of evolutionary rate will apply to different tumor types.

Sequence variations may be represented by a variety of mutational changes, for example and without limitation, the overall number of nucleic acid sequence substitutions in the tumor sequencing data as compared to normal or reference sequence data; the number of one or more specific nucleic acid sequence substitutions, including one or more of the following specific nucleic acid sequence substitutions: A→T, A→C, A→G, T→A, T→C, T→G, C→A, C→T, C→G, G→A, G→T, or G→C in the tumor sequencing data as compared to normal or reference sequence data; and/or the number of gene mutations in the tumor sequencing data. The number of gene mutations may be limited to mutations found in driver genes implicated in cancer, such as, without limitation, those genes listed in the "Genetics" column of Table 1, or listed in the COSMIC1 database, or in the Cancer Gene Census, e.g., Tier 1, or Tier 1 and Tier 2 (cancer-.sanger.ac.uk/census). The value also may be a quantification of specific types of mutations, such as the number of copy-number alterations, potentially subdivided by classes such as over and/or below a value ranging from 100,000 to 1,000,000 nucleotides in length, e.g., 500,000 nucleotides in length. Another class of mutation type covered is structural variations (SVs) involving gain, loss, or rearrangement of DNA, which may also be further subdivided by scale or likely molecular mechanism. Of note, the quantitative measure of evolutionary rate does not focus on any specific "driver" genes, but on the general rate of mutation in the tumor or in specific regions or classes of genomic material in the tumor genome.

In one non-limiting example of a variant calling module, Weaver is a computational method to identify allele-specific copy number of SVs (ASCN-S) as well as the inter-connectivity of them in aneuploid cancer genomes. The methodological contributions of Weaver are trifold: (i) the method provides a quantitative copy number measurement of SVs in an allele-specific manner; (ii) it estimates the phasing of SVs using NGS data; (iii) the method generates highly accurate base-pair resolution ASCN-G profiling in aneuploid cancer genomes by simultaneously achieving (i) and (ii). Weaver is described in additional detail in Li et al. (Li, Y., Zhou, S., Schwartz, D. & Ma, J. Allele-specific quantification of structural variations in cancer genomes. *Cell Syst.* 2016 Jul. 27; 3(1): 21-34. doi:10.1016/j.cels.2016.05.007).

The input of Weaver is a BAM file of aligned and unaligned reads from a particular cancer sample. If there is matched normal sample available, it can also be used. A BAM file (.bam) is the binary version of a SAM file. A SAM file (.sam) is a tab-delimited text file that contains sequence alignment data. The first step is to call variants (including both SNPs and SVs) based on the BAM file. The framework is flexible and allows users to choose their own variant calling tools. The detailed description for preparing Weaver input is in the Supplemental Experimental Procedures of Li et al. In contrast to existing methods, Weaver quantifies the copy number of SVs in an allele-specific manner (i.e., ASCN-S), thus providing useful information to help infer when the SV happened relative to the chromosome duplication (i.e., timing of SV).

In further examples, Weaver performs allele-specific SV calls from WGS data, added to SNV+CNV calls. SVs include changes in DNA content or order including duplication or loss, inversion, or translocation of genetic material. In another example, TCGA may make SNV+CNV calls from MuSE, MuTect2, VarScan2, and/or SomaticSniper.

Evolution Modeling Module

Tumor phylogeny algorithms or modules infer a phylogenic tree of tumor cells from sequence data and mutations present in tumor cells when compared to normal cells or a reference sequence. A variety of tumor phylogeny algorithms are known in the art. In one aspect, the tumor phylogeny algorithm is that of TUSV phylogeny software (Eaton et al., Eaton, J., Wang, J. & Schwartz, R. Deconvolution and phylogeny inference of structural variations in tumor genomic samples. *Bioinformatics* 34(13), i357-i365 (2018)). In another aspect, the tumor phylogeny algorithm is that of the Canopy tool (Jiang et al., Jiang, Y., Qiu, Y., Minn, A. J. & Zhang, N. R. Assessing intratumor heterogeneity and tracking longitudinal and spatial clonal evolutionary history by next-generation sequencing. *Proc. Nat'l. Acad. Sci. U.S.A.* 113, E5528-E5537 (2016), providing details of the Canopy model, and also describing additional cancer clonal phylogeny reconstruction models). Additional details regarding the TUSV phylogeny software and the Canopy tool are provided below, and in the cited Jiang et al. and Eaton et al. references.

Prior to the machine learning step, features are extracted from the tumor phylogeny tree model and directly from variant calling data. Phylogenic tree information is information extracted from or characterizing a phylogenic tree inferred as described above. Non-limiting examples of phylogenic tree information includes: the number of clones in the phylogeny tree; the number of single-nucleotide variations, copy-number alterations, and/or structural variations in the largest clone and/or the smallest clone of the phylogeny tree; the mean, maximum, minimum, and/or variance in the number of mutations along the path between two leaf nodes of the phylogeny tree; the number of mutations required from the root node to a leaf node of the phylogeny tree; the maximum number of single-nucleotide variations, copy-number alterations, and/or structural variations in a clone of the phylogeny tree; and/or the total number of single-nucleotide variations, copy-number alterations, and/ or structural variations in the phylogeny tree.

Machine Learning Module

In general, machine learning builds new and/or leverages existing algorithms to learn from data, in order to build generalizable models that give accurate predictions, or to find patterns, particularly with new and unseen similar data. Machine learning takes training data sets and, through use of, for example, statistical and mathematical modeling algorithms, is able to provide an output that either classifies data to provide a specified output or clusters data for discovering the composition and structure of the data. In the context of the present disclosure, the machine learning component may conduct classification predictive modeling or regression predictive modeling to produce output, such as survival at a given time point in the future, risk of metastasis, expected lifespan, such as a Kaplan Meier survival curve or estimation, or a classification of a group of patients into cohorts. Machine learning may include deep learning to progressively extract higher level features from the raw input.

Machine learning components or modules comprise one or more algorithms, as are broadly-known, which are selected and assembled into the larger machine learning module based upon a variety of factors, including, for example and without limitation, the type of data to be used for training and to be evaluated after training and the desired output of the machine learning component. As part of the training process, the data set is split, and part of the data set is used for training, and another part of the data set is used for testing the machine learning component. As seen in the examples below, the choice of algorithm or mathematical models, along with the choice of data, will determine the strength of the machine learning component. For example and without limitation, regression algorithms include: simple or multiple linear regression, decision tree or forest regression, artificial neural networks, ordinal regression, Poisson regression, or nearest neighbor methods. As shown below, in one non-limiting example, Cox regression (proportional hazards regression) is selected as being an appropriate algorithm component for survival analysis and prediction, and providing a suitable output, e.g., a curve, for patient survival. Other potentially useful algorithms include Random Forest (RF) and support vector machine (SVM) algorithms. Although specific algorithms are described in the examples below as being useful in the methods and systems described herein, other algorithms may be used to optimize the machine learning process (see, e.g., Wang, P. et al. (2017). Machine Learning for Survival Analysis: A Survey. ACM Computing Surveys. 51. 10.1145/3214306). In one non-limiting example, the machine learning module is implemented using lifelines, an implementation of survival analysis in Python. In another example, the machine learning is implemented in scikit-learn in Python. In one example, the machine learning applies Cox regression, support vector machine (SVM), or random forest (RF) algorithms to the features, e.g., characterizing sequence variation, such as single nucleotide variations, copy-number alterations, and/or structural variations in the tumor cell sequences, such as the rates of accumulation of such features overall, or at any stage in the tumor phylogenic tree. The machine learning methods may include variants with regularization or feature selection, techniques that may increase robustness by identifying most informative subsets of the input feature set.

In one embodiment, the machine learning method provided herein can be implemented to provide survival prediction, or a risk of metastasis, relative to a choice of therapeutic mode, such as primary therapy or adjuvant therapy, agent, such as chemotherapy, radiation therapy, immunotherapy, or specific examples of such therapies, and timing of treatments. For example, the training data may include data relating to timing of administration of a specific anticancer therapeutic, such as, without limitation doxorubicin or other chemotherapeutic active agents as primary or adjuvant therapy.

In one embodiment, both a two-node tumor phylogeny tree, implementing a simplified model of tumor evolution comprising a single ancestral and a single tumor clone, and a complex phylogeny tree potentially describing multiple related tumor clones are produced at the evolution modeling stage, and features are extracted from those models and are processed in the machine learning step. It will be understood that a "phylogeny tree" refers to and describes any data structure and representation of the relationship between inferred clones or nodes. In one embodiment, the machine learning classifies or stratifies a group of patients into two or more cohorts based on survival, such as a Kaplan Meier estimation, risk of metastasis, and/or risk of drug resistance.

In non-limiting embodiments, a system and method for cancer prognosis includes at least one computer system having at least one processor in communication with at least one data storage device. The computer system may execute one or more software applications stored locally on or remotely from the computer system. The software applications may be in the form of program instructions stored on one or more non-transitory computer-readable mediums that, when executed by the processor, perform one or more steps, actions, or functions. In some non-limiting implementations, the software application may execute on one or more servers as Software-as-a-Service (SaaS) and be accessible to a user through one or more webpages and/or client applications. Various other arrangements are possible.

It will be appreciated that various machine learning and artificial intelligence techniques may be used. As described herein, a machine learning system may be constructed and trained based on the tumor phylogenetic tree information such as sequence variations, and clinical, driver gene, or polymorphism information. Machine learning techniques used to train a data set and process patient data may include, for example, supervised and/or unsupervised techniques, such as decision trees, gradient boosting, logistic regressions, artificial neural networks, Bayesian statistics, learning automata, Hidden Markov Modeling, linear classifiers, quadratic classifiers, association rule learning, or the like.

Additional patient data or features may be employed in the machine learning step along with the phylogenic tree features. These additional data may include clinical features. A clinical feature is one or more feature that relates to a patient's demographics and clinical history. The clinical feature may be a patient demographic value, for example and without limitation: patient age, gender, ethnicity, race, menopause status, or any other pertinent demographic value. Clinical features also may include items of a patient's history, such as neoplasm cancer status, age at initial pathological diagnosis, margin status, or history of neoadjuvant treatment. Clinical features also include pathological or laboratory test results. For example and without limitation, in the case of breast cancer, such clinical features may include her2 neu chromosome 17 signal ratio value, her2 immunihistochemistry (IHC) results, number of positive lymph nodes by H&E (hematoxylin and eosin) staining, her2 erbb positive finding, results of in situ hybridization of chromosome 17, breast carcinoma progesterone receptor status, breast carcinoma estrogen receptor status, results of MC for cytokeratin as a micrometastasis indicator, her2 in situ results, or her2 neu receptor IHC results.

Non-phylogenetic genomic features also may be included in the machine learning process. Such genomic features may include one of more cancer driver genes or their mutations, such as driver gene polymorphisms, for example, single-nucleotide polymorphisms (SNPs), e.g., polymorphisms or copy number variations associated with cancers. Driver features, e.g., driver-centric genomic features, can be genetic, coding or non-coding, or epigenetic in nature, and often differ between cancer types. Driver features include mutations or polymorphisms in genes that are associated with a cancer type, and may include the presence of cancer-associated SNPs or copy-number alterations. Driver features may be and are typically identified during the sequencing process, but may be identified by other methods, such as by quantitative PCR, immunochemistry or IHC, in situ staining, hybridization methods, or any other suitable laboratory or clinical procedure or assay that identifies genotypic and/or phenotypic variations associated with a cancer.

Implementation of the methods and systems described herein involve training the machine learning module on a suitable data set, and in embodiments validating the training prior to implementation. As such, a computer system may be characterized as being "trained" once the training phase has ended and test data is successfully run using the system, and the system is adequately validated. As one of ordinary skill would recognize, based on the present disclosure, the choice of data, software modules, either off-the-shelf or customized and optimized for the systems described herein, and output may be further optimized. Training data sets are available publicly, or may be developed privately. As indicated below, Cancer Genome Atlas (TCGA) data, including genomic sequencing data, may be used for training, testing, and validation.

EXAMPLE 1

A variety of lines of evidence have suggested that these distinct hypermutability phenotypes are not merely a curiosity but have important implications for how a tumor is likely to evolve in the future. For example, it has been shown that tumors prone to whole-genome duplications (WGD) have significantly worse prognosis than similar tumors prone only to focal copy-number alterations (CNAs). Similar observations have appeared anecdotally for a variety of specific mutation classes. The present work was intended to explore a key implication of these past studies: how a tumor is likely to progress in the future is influenced by, and in principle predictable from, how it has evolved so far. That is, the patient-specific spectrum of mutational phenotypes acting in a given tumor has predictive power over its future progression. This approach is distinct from, and complementary to, the standard "driver gene" model of prediction that is the basis of most current work in genomic diagnostics for cancer. We specifically develop this idea by proposing that by applying "tumor phylogenetics," the reconstruction of the history of cell lineages in a cancer, we can reconstruct not just a tumor's current state but the mechanisms by which it got there. The combination of mechanisms of mutation and the degrees to which they act in a given cancer would then, we propose, have independent predictive power for future progression that we can harness via machine learning.

The following implements and demonstrates an example of this idea of progression prediction from somatic hypermutability phenotypes. Below, we describe a general model for implementing this idea and specific variations intended to work with whole exome sequence (WES) and whole genome sequence (WGS) data. We then demonstrate the effectiveness of this strategy via validation on Cancer Genome Atlas (TCGA) data from breast invasive carcinoma (BRCA) and lung adenocarcinoma (LUAD), showing in each case that prediction from phylogeny-derived mutator phenotype profiles has significant predictive power for survival and recurrence-free survival complementary to that derivable from driver-centric genomic profiling or more traditional clinical predictors of prognosis.

Pipeline: FIG. 1 summarizes the overall process of model training and classification. We assume the process begins with genomic sequence data, which we assume here may be WES or WGS, and either single- or multi-sample. These data are preprocessed and passed to one or more variant callers, ideally including single nucleotide variants (SNVs) and CNA calls as well as calls for diverse classes of structural variations (SVs) to produce a variant call format (VCF) file identifying variants and their variant allele frequencies (VAFs) per sample. These variant calls are then passed as input to a tumor phylogeny algorithm, used to infer one or more clonal evolutionary states and a cellular lineage tree connecting them. Next, a feature selection stage is used to extract a variety of quantitative measures of evolutionary rate corresponding to distinct mutation mechanisms intended to approximate the degree to which distinct mutator phenotypes act in a tumor. These features may be supplemented by additional clinical features provided as input as well as driver-centric genomic features. Feature selection is then followed by training or applying a machine learning classification algorithm for prediction of a phenotype of interest labeled in the training data. We describe each of these steps in more detail below.

Data Preprocessing: For the three different variants, both SNVs and CNAs are downloaded from TCGA Genomic Data Commons Data Portal (GDC), while SVs are called using Weaver (Li, Y., Zhou, S., Schwartz, D. & Ma, J. Allele-specific quantification of structural variations in cancer genomes. *Cell Syst.* 2016 Jul. 27; 3(1): 21-34. doi: 10.1016/j.cels.2016.05.007). For each cancer sample, the three variants are integrated and converted into a single Variant Call Format (VCF) file, which is the input format required by Canopy and TUSV. Canopy uses SNV and CNV data to predict tumor phylogeny, while TUSV is based on CNVs and SVs. Since Weaver requires WGS data to call SVs, the shortage of WGS data greatly limits the number of samples that can be used in TUSV. Therefore, we classify two groups of samples for both BRCA and TUSV. The first group has data of all three variants, which can be used by both Canopy and TUSV. The other group only contains SNV and CNA information, which can only be used by Canopy.

Clinical features were extracted from TCGA-reported clinical metadata extracted from GDC. We directly remove all clinical features for which fewer than half of the samples are available. We then manually pruned to identify a set of features intended to provide a consensus representation of information likely to be available to clinicians at the time of diagnosis. The final list of included features is provided in Table 1. The features are preprocessed in proper ways to fit into the Cox regression model. We categorize all features into 3 parts: multinomial feature, pseudo multinomial features, and continuous feature binary feature.

Phylogeny trees: We show two types of paradigm to build up phylogeny trees, based on our availability of whole genome sequencing (WGS) versus whole exome sequence (WES) data. Our approach is intended to capitalize specifically on the broader SV variant classes enabled by WGS data. We use an extension of our TUSV phylogeny software to demonstrate the approach in that situation. However, we further demonstrate the software with the third-party Canopy tool to provide a point of comparison when only WES data is available. Finally, we provide a third point of comparison, using a trivial phylogeny model, which we dub the two-node phylogeny, consisting of a diploid reference "normal" root and a single derived cancer state.

Canopy is able to identify the subclones and predict the phylogeny tree based on an input VCF file specifically combining SNV and CNA data for inference, making it suitable for WES data. First, the clonal decomposition is explored by Markov chain Monte Carlo (MCMC) simulation, and optimized based on maximum likelihood estimation (MLE). Users need to specify the range for the number of subclones to deconvolute, and also the range for the number of chains and the length of each chain for MCMC simulation. Bayesian information criterion (BIC) is used to determine the optimal number of clones in the specified range. The clonal composition and the bifurcating tree with SNVs and CNAs on the edges are selected based on posterior distribution. Canopy outputs the clonal composition and phylogenetic trees, with each SNV or CNA assigned to a specific edge, which are then extracted as phylogeny features.

Tumor phylogenetic reconstruction by TUSV employs a different algorithm, which optimizes for a likelihood model via a constrained optimization algorithm. TUSV is designed for phylogenetic inference from CNVs and SVs. It formularizes the phylogeny prediction as a mixed-integer linear programming (MILP) problem. This model has a trade-off between the likelihood of both CNVs and SVs described in observed breakpoints, and the evolutionary cost of the phylogenetic tree. The optimal clonal decomposition and the phylogeny tree is found by performing a coordinate descent algorithm on this MILP system. We extended the previously published TUSV for this work to further handle SNVs through a simplified mutation model excluding the possibility of recurrent mutation but allowing for loss of SNVs through allelic loss. The output of this analysis is a set of clones, characterized by the subset of mutations inferred in each, and a phylogeny connecting those clones.

We finally examined the two-node phylogeny model. This is intended as a trivial baseline model of phylogenetics for which we assume that there is a single branch of evolution from normal to cancer, resulting in a tree of two nodes and one edge. This is intended to give a crude approximation to evolutionary trajectories that makes minimal assumptions about evolutionary model and data types.

Feature extraction: Twenty features are extracted from the evolutionary trees from Canopy [Table 1, "2node Phylogenetic" and "Multi-node Phylogenetic" columns]. Features in the 2node phylogenetic column count the number of different type of SNVs. The tree information is represented by clonal composition of SNVs and CNAs, variants count, distance, and height. Distance is defined as the number of mutations along the path between two leaf nodes. Height refers to the number of mutations required from the root node to a leaf node. We also set subdivide CNVs by a distance threshold for the CNV region in our samples, providing phylogeny features indicating whether the size of CNV regions exceeds 500,000 nucleotides (NT).

TABLE 1

| | Clinical | Driver | 2node Phylogenetic | Multi-node Phylogenetic |
|---|---|---|---|---|
| 1 | age at initial pathologic diagnosis | SPEN | A → T | clone number |
| 2 | her2 neu chromosome17 signal ratio value | ARIDIA | A → C | SNV counts in the largest clone |
| 3 | her2 immunohistochemistry level result | LRP1B | A → G | SNV counts in the smallest clone |
| 4 | number of lymphnodes positive by he | PIK3CA | T → A | CNV counts in the largest clone |
| 5 | her2 erbb pos finding cell percent category | ESR1 | T → C | CNV counts in the smallest clone |
| 6 | fluorescence in situ hybridization diagnostic procedure chromosome 17 signal results | KMT2C | T → G | mean distance |
| 7 | gender | GATA3 | C → A | maximum distance |
| 8 | history of neoadjuvant treatment | PTEN | C → T | minimum distance |
| 9 | ethnicity | KMT2D | C → G | variance of distance |
| 10 | person neoplasm cancer status | TBX3 | G → A | maximum height |

TABLE 1-continued

| | Clinical | Driver | 2node Phylogenetic | Multi-node Phylogenetic |
|---|---|---|---|---|
| 11 | breast carcinoma progesterone receptor status | RB1 | G → T | minimum height |
| 12 | cytokeratin immunohisto-chemistry staining method micrometastasis indicator | FOXA1 | G → C | maximum SNV counts |
| 13 | lab procedure her2 neu in situ hybrid outcome type | AKT1 | total SNV counts | maximum CNV counts |
| 14 | race | CDH1 | total CNV counts | |
| 15 | menopause status | TP53 | total SV counts | |
| 16 | margin status | MAP2K4 | CNV region over 500,000 NT | |
| 17 | breast carcinoma estrogen receptor status | NCOR1 | CNV region below 500,000 NT | |
| 18 | lab proc her2 neu immunohis-tochemistry receptor status | NF1 | | |
| 19 | | ERBB2 | | |
| 20 | | RUNX1 | | |

Table 1: Features from the clinical data, driver gene data, and phylogeny tree. We only display the important clinical features selected for BRCA samples. For phylogenetic and other genetic features, the whole lists are shown in this table.

In addition, we also collect other driver-centric genetic features, shown in Table 1, "Driver" column. We also count the number of gene mutations observed in the sample, referring to COSMIC1 (Catalogue Of Somatic Mutations In Cancer). The clinical features are directly downloaded from TCGA GDC. We only display the important features selected for BRCA as an example [Table 1, "Clinical" column].

Cox Regression: The clinical prognoses of cancer patients such as survival time and metastasis (disease free survival) are censored data, i.e., the death event or recurrence of some samples are not observed due to limited follow up time. In our case of breast cancer and lung cancers, only a small proportion of samples are observed to be deceased within the available follow-up time. Therefore, we do not go for the normal binary classification methods. Instead, we perform Cox regression on these censored data, which is specifically designed to cope with the challenges of censored data. Cox regression is a semi-parametric regression method based on the proportional hazards assumption:

$$h_i(t) = h(t)e^{\beta^T x_i},$$

where $h_i(t)$ is the hazard of patient i at time t, h(t) is the non-parametric part calculated from the training data, $x_i$ is the feature vector of sample i, $\beta$ is the parameter to be estimated by regression. The hazard function of patient is defined as:

$$h_i(t) = \lim_{\Delta t \to 0} \frac{Pr(t < T_i \leq t + \Delta t \mid T_i > t)}{\Delta t},$$

where $T_i$ is the decease time of patient i. It means the probability of death if the patient has survived to time point t. Instead of predicting whether the patient will be dead or alive, cox regression estimates the $\beta$, and thus provide the hazard of patient:

$$h_i(t) = h(t)e^{\beta^T x_i}.$$

When the total number of samples is large enough, we can roughly take the h(t) to be similar during the cross-validation. The comparison of $h_i(t)$ thus reduces to comparison of surrogate hazard:

$$\eta_i = \beta^T x_i.$$

Evaluation: With the predictions of surrogate hazard $\eta$s, we evaluate prediction results based on an assessment of concordance index (CI), and an assessment of statistical significance of separating censored survival data based on a logrank test.
The CI is defined as follows:

$$CI = \frac{\Sigma_{i,j} \mathbb{1}_{T_i > T_j} \mathbb{1}_{\eta_i < \eta_j} \delta_j}{\Sigma_{i,j} \mathbb{1}_{T_i > T_j} \delta_j}$$

$\delta_j=1$ means that sample j is observed to be dead, and $\delta=0$ means the sample j is alive till last follow up. It is a value similar to AUC, which reaches perfect prediction when CI=1 and random guess when CI=0.5.

The logrank test provides a statistical test to accept or reject the null hypothesis $\mathcal{H}_0$: two groups of samples share same survival profile. It calculates statistic $Z^2$ from observations of two groups of censored data, while $$Z \xrightarrow{d} N(0, 1),$$

leading to p-value to accept/reject. In our experiments, we classify all samples into two groups with the median of surrogate hazards $\eta$s, and use logrank test to evaluate the differences between these two groups of malignant and benign samples. The Cox regression, logrank test are implemented using Python package lifelines.

We implement the step-wise feature selection of clinical features, driver features, and phylogenetic features using 10-fold cross validation, whose optimization goal is to maximize the CI of predictions on the validation sets. Specifically, clinical features are selected step wise to maximize CI, then driver features or phylogenetic features are selected step wise to maximize CI. At the evaluation stage, CI, statistic ($Z^2$) and p-value are calculated for comparison of different sets of features.

Feature Correlation: The evaluation of correlation between features works as a validation step for the step-wise feature selection. It also contributes to the identification of orthogonal features and provides biological insights to each feature. We first perform basic feature selection steps including the removal of zero-variance features and the exclusion of zero-mutual-information features. Next, we use hierarchical clustering based on UPGMA distance calculate to classify the filtered feature sets. This clustering gives the optimal number of clusters and the corresponding cluster compositions, which are used as parameters to generate a heatmap showing Pearson Correlation between each pair of those features.

Results

Figure 3:
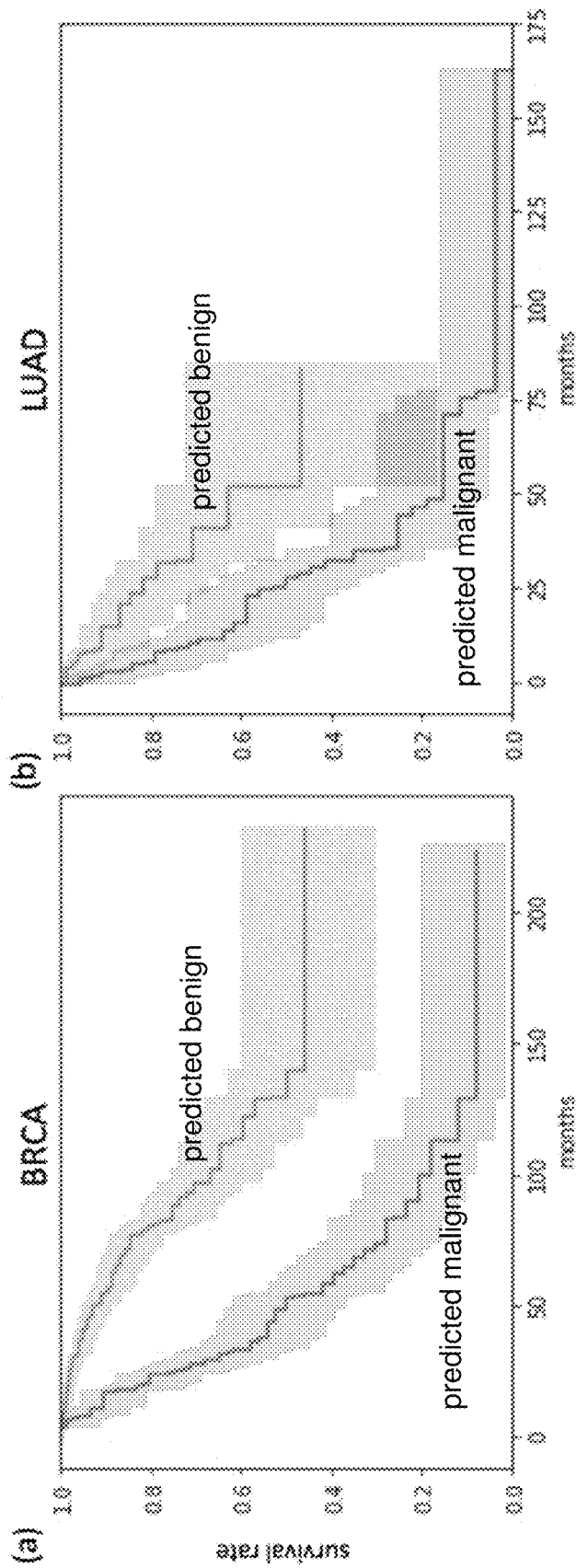
FIG. 3: Kaplan Meier estimators of predicted malignant and benign samples of BRCA (a) and LUAD (b) samples using both clinical features and phylogenetic features. Patients are classified into two groups: malignant and benign based on the predicted hazards. Samples with hazards larger than the median of predicted hazards are classified as malignant, otherwise as benign. Logrank test is then conducted on the two groups, where p-value=2.4e-11 for BRCA, and p-value=8.8e-08 for LUAD, showing significant distinct survival profiles.

Feature Correlation: We evaluated the feature correlation for clinical and driver features, with the phylogenetic features extracted from evolution prediction based on the 2-node phylogeny algorithm. We performed this analysis on the dataset of 1044 samples of BRCA with SNVs and CNAs. FIG. 3 of U.S. Provisional Patent Application No. 62/838,649, filed Apr. 25, 2019, which is incorporated herein by reference in its entirety, and to which this application claims priority, shows the Pearson correlations between features, noting that there are four positively related blocks and the boxes, corresponding approximately to features characterizing point mutation processes, those characterizing clinical data, those characterizing copy number and other structural variation processes, and those corresponding to driver gene mutation processes, showing a strong positive correlation across gene mutations, gene deletion and gene amplification. Those genes are collected from COSMIC. We also see confirmation that the deletions of genes are negatively correlated to the amplification of those genes. In addition, the data show cross-correlations between feature classes, for example, in showing that driver mutation features are correlated with both general point mutation rate and general copy number mutation rate processes.

Performance of prognoses prediction: Table 2 summarizes prediction results across method variants and in comparison to clinical predictors alone. FIG. 3 illustrates the separation by survival time between predicted malignant and predicted benign tumors. In each case, we would expect that clinical predictors should provide the strongest predictive information and do indeed find that to be the case, as assessed by CI and p-value. We are primarily interested in establishing whether phylogenetic features enhance predictive value and find that they do so.

Figure 4:
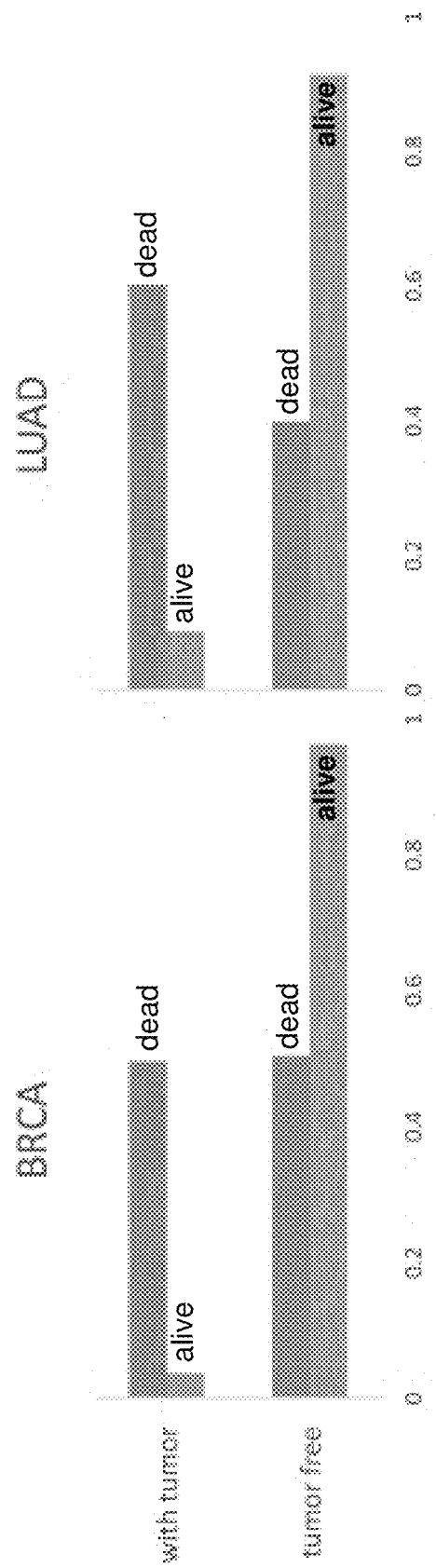
FIG. 4: Conditional distribution of "person neoplasm cancer status" in live and deceased patients of BRCA and LUAD samples. It exhibits distinct distribution in the survival status: the deceased patients contain a much larger portion of samples with tumors, indicating that "person neoplasm cancer status" is a strong feature for our regression model (although we do note that the alive samples are alive till the last follow up time point).

We find for LUAD that clinical features outperform 2-node or multi-node prediction by both CI and log-rank score, but that clinical+phylogenetic features outperform clinical alone. Clinical+multinode phylogenies proved the strongest combination by both measures. The clinical feature "person neoplasm cancer status" (whether the patient is tumor free or with tumor) is the strongest clinical feature and can significantly improve the performance of our model but potentially unreasonable to treat as available for clinical use. We are interested how the model behaves without it; see FIG. 4. We further tested the removal of this clinical feature. In the absence of that feature, we find a qualitatively similar result that clinical predictive value is still superior to phylogeny alone, although to a lesser degree, but both clinical+phylogeny feature combinations outperform clinical alone by both measures.

BRCA showed qualitatively similar results. In this case, clinical features were the most strongly predictive feature set by themselves but clinical+phylogenies were the strongest predictors overall. For the full clinical feature set, clinical+2-node features proved most predictive while for the reduced clinical feature set, clinical+2-node improved CI but led to somewhat worse log-rank statistic.

TABLE 2

| Features | BRCA (WES) | | LUAD (WES) | |
|---|---|---|---|---|
| | OS | DFS | OS | DFS |
| clin | 83.1 | 79.5 | 71.9 | 68.4 |
| driver | 57.1 | 55.8 | 58.4 | 56.5 |
| 2node | 58.1 | 53.6 | 52.7 | 58.3 |
| muiltinode | 54.9 | 54.2 | 54.9 | 52.4 |
| clin + driver | 83.8 | 80.4 | 72.8 | 68.8 |
| clin + 2node | 83.2 | 80.2 | 71.9 | 69.1 |
| clin + muiltinode | 83.2 | 79.2 | 72.3 | 68.3 |
| clin + all_genomics | 83.9 | 80.6 | 73.0 | 69.1 |
| clinΔtumor | 76.9 | 69.1 | 69.6 | 62.9 |
| clinΔtumor + driver | 77.7 | 70.1 | 70.3 | 66.1 |
| clinΔtumor + 2node | 77.2 | 69.3 | 69.9 | 66.3 |
| clinΔtumor + muiltinode | 76.9 | 69.2 | 69.8 | 64.0 |
| clinΔtumor + all_genomics | 78.3 | 71.9 | 71.1 | 66.8 |

Table 2: Overall survival (OS) and disease-free survival (DFS) prediction with different sets of features on the BRCA and LUAD samples as measured by the CI test. Driver and phylogenetic features are extracted from 2node and multinode phylogeny trees separately. Clinical features always perform best among all the three feature sets. However, adding the features from 2node and multinode phylogeny trees can always improve the performance of CI test. When the most informative clinical feature ("person neoplasm cancer status": tells whether tumor free or with tumor) is removed, the performances suffer, while the additional 2node and multinode features is still synergistic to the prediction of hazards. These experiments indicate that the additional genomic features and phylogeny features are able to provide some orthogonal features to clinical features and improve the prognoses prediction.

Best features: We collected the selected features that lead to best performance in Table 2. Specifically, the selected clinical and genomic features that lead to optimal performance in "clin+2node" experiments, and clinical and phylogenetic features that lead to optimal performance in "clin+multinode" experiments. The complete list and rank can be found in Table 3.

TABLE 3

Selected clinical, genomic, and phylogenetic features for predicting hazards of patients

| | Selected clinical features (BRCA) | | Selected clinical features (LUAD) |
|---|---|---|---|
| 1 | person neoplasm cancer status | 1 | person neoplasm cancer status |
| 2 | age at initial pathologic diagnosis | 2 | pathologic stage |
| 3 | pathologic stage | 3 | age at initial pathologic diagnosis |
| 4 | breast carcinoma progesterone receptor status | 4 | histological type |
| 5 | breast carcinoma estrogen receptor status | 5 | history of neoadjuvant treatment |
| 6 | lab proc her2 neu immunohistochemistry receptor status | 6 | race |
| 7 | menopause status | | |
| 8 | cytokeratin immunohistochemistry staining method micrometastasis indicator | | |
| 9 | margin status | | |

| | Selected driver features (BRCA) | | Selected driver features (LUAD) |
|---|---|---|---|
| 1 | PIK3CA | 1 | ERBB2 |
| 2 | LRP1B | 2 | ESR1 |
| 3 | FOXA1 | 3 | KMT2D |
| | | 4 | PTEN |
| | | 6 | PIK3CA |
| | | 7 | TBX3 |

| | Selected 2node phylogenetic features (BRCA) | Selected 2node phylogenetic features (LUAD) |
|---|---|---|
| 1 | G → T | |
| 2 | CNV region over 500,000 NT | |
| 3 | CNV deletion | |

| | Selected multi-node phylogenetic features (BRCA) | Selected multi-node phylogenetic features (LUAD) |
|---|---|---|
| 1 | CNV counts in the smallest clone | |

The top two features in both breast cancer and lung cancer: "person neoplasm cancer status" reports whether the patient has tumor or is tumor free. The cancer is significantly more optimistic when no tumor is observed in general. The "age at initial pathologic diagnosis" is the second feature for BCRA and third for LUAD and is also highly correlated to the severity of the cancer. Since the tumor is caused by the accumulation of somatic alterations, the older the patient, the more likely is the patient to suffer from tumors. Older age also indicates worse health conditions and inferior prognosis. The third clinical feature for BRCA and second for LUAD is pathologic stage, which is examined by pathologist on the tumor microscopically and provides informative clue of cancer growing and spreading.

There are 10 driver features and 4 phylogenetic features selected by BRCA and LUAD separately. The top 3 genomic features for BRCA are genomic aberrations of gene PI3KCA (Phosphatidylinositol-4,5-bisphosphate 3-Kinase Catalytic Subunit Alpha), LRP1B (Low-Density Lipoprotein Receptor-Related Protein 1B), and FOXA1 (Forkhead Box A1) all of which have been proposed by previous research are closely related with cancer progression. The genomic features for LUAD is ERBB2 (Erb-b2 Receptor Tyrosine Kinase 2), ESR1 (Estrogen Receptor 1), KMT2D (Lysine Methyltransferase 2D), PTEN (Phosphatase and Tensin Homolog), SPEN (Spen Family Transcriptional Repressor), PIK3CA, and TBX3 (T-box 3), all of which have been previously implicated in cancer development and progression.

One selected phylogenetic feature for BRCA is the CNV counts in the smallest clone of the tumor tissue, although none were selected for LUAD. The three other selected phylogenetic features refer to rates of specific kinds of point or copy number mutations.

Additional Work

Incorporate SV, SNV, and CNV data simultaneously in our phylogeny predictions, because SVs have a major contribution to the tumor evolution. TUSV is used as the tool currently used to reconstruct tumor phylogeny based on CNVs and SVs, described as breakpoints in the input file. The performance of Canopy, TUSV, and Two-nodes are compared, as they utilize different variants input and algorithms.

More features may be extracted from the predicted evolutionary trees because the current phylogeny features provide small improvement in addition to the clinical and driver features we want to extract. These may include further elaboration on rates of distinguishable sub-classes of SV, CNV, or SNV, as well as signatures of other specific mutation processes or other aggregate features of the tumor evolution processes.

Other machine learning methods for preprocessing, feature selection, and classification or regression on data may be applied. These might include other strategies for regularization, such as LASSO, alternative strategies for feature selection, or different classification or regression methods, such as via deep learning.

Data from other cancer types including Head and Neck Squamous Cell Carcinoma (HNSC) also may be analyzed. The comparison of analysis across different cancer types is expected to improve the reliability of our results. This also evaluates the different tumor evolution mechanisms of each cancer type.

Additional prediction frameworks, including the metastasis prediction may be added. The metastasis strongly relates to the patient survival and disease relapse. The prediction of metastasis based on the tumor progression is expected to assist in both cancer research and clinical studies.

Examining larger patient cohorts, especially larger cohorts of WGS data.

Examining other progression outcomes, such as response to therapeutics.

EXAMPLE 2

Two variants of the pipeline were successfully executed:

TCGA features→2-node phylogeny→ML prediction for 124 WES samples, and

Weaver features→TUSV phylogeny→ML prediction for 41 WGS samples.

Two ML predictors were used: Random Forest (RF) and Support Vector Machine (SVM). SVM appeared to be more effective.

Of Note:

Genomic (primarily phylogenetic) features are at least competitive with clinical features; and SVs and resulting improved phylogenies appear to be helpful for prediction.

Figure 5:
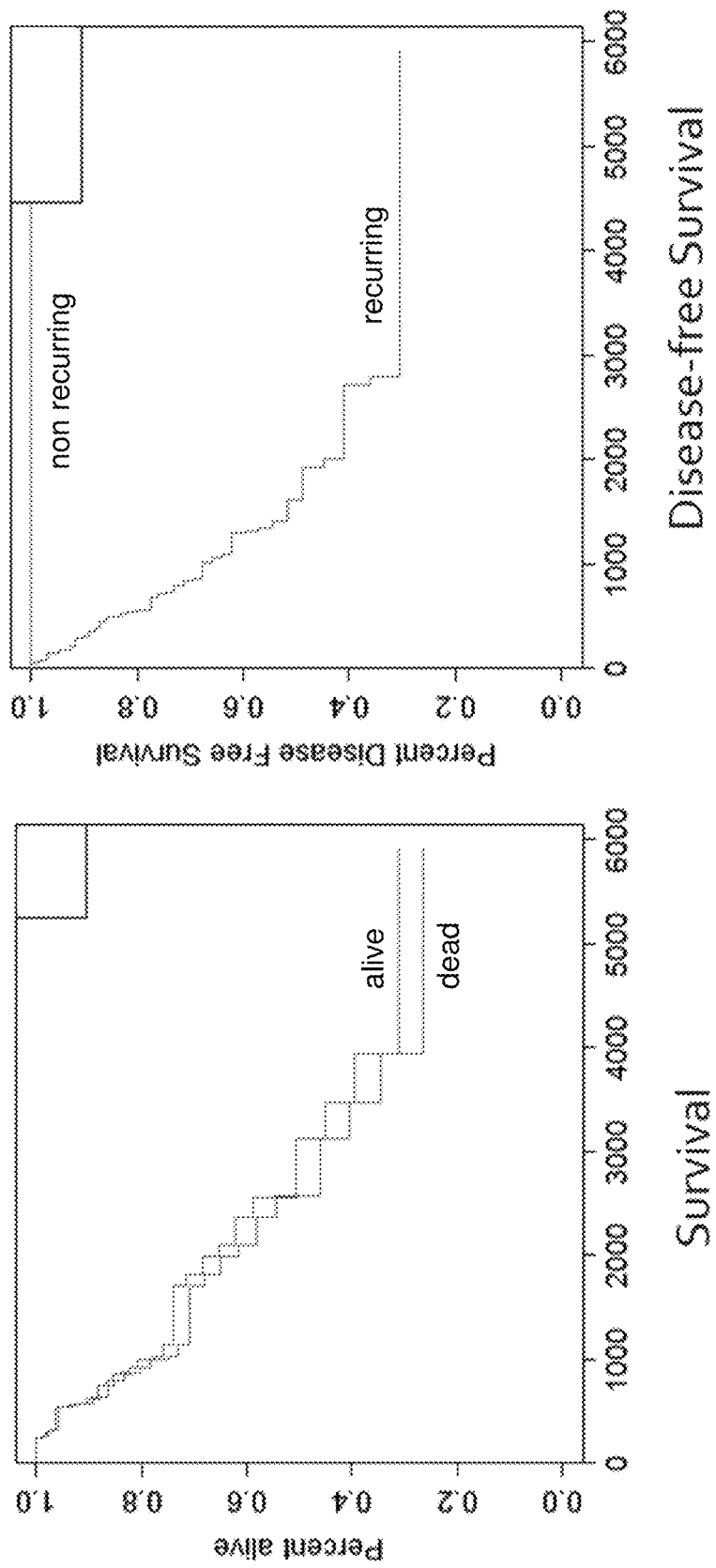
FIG. 5 provides graphs showing survival curves for Two-Node Phylogeny WES Predictions by SVM.
Figure 6:
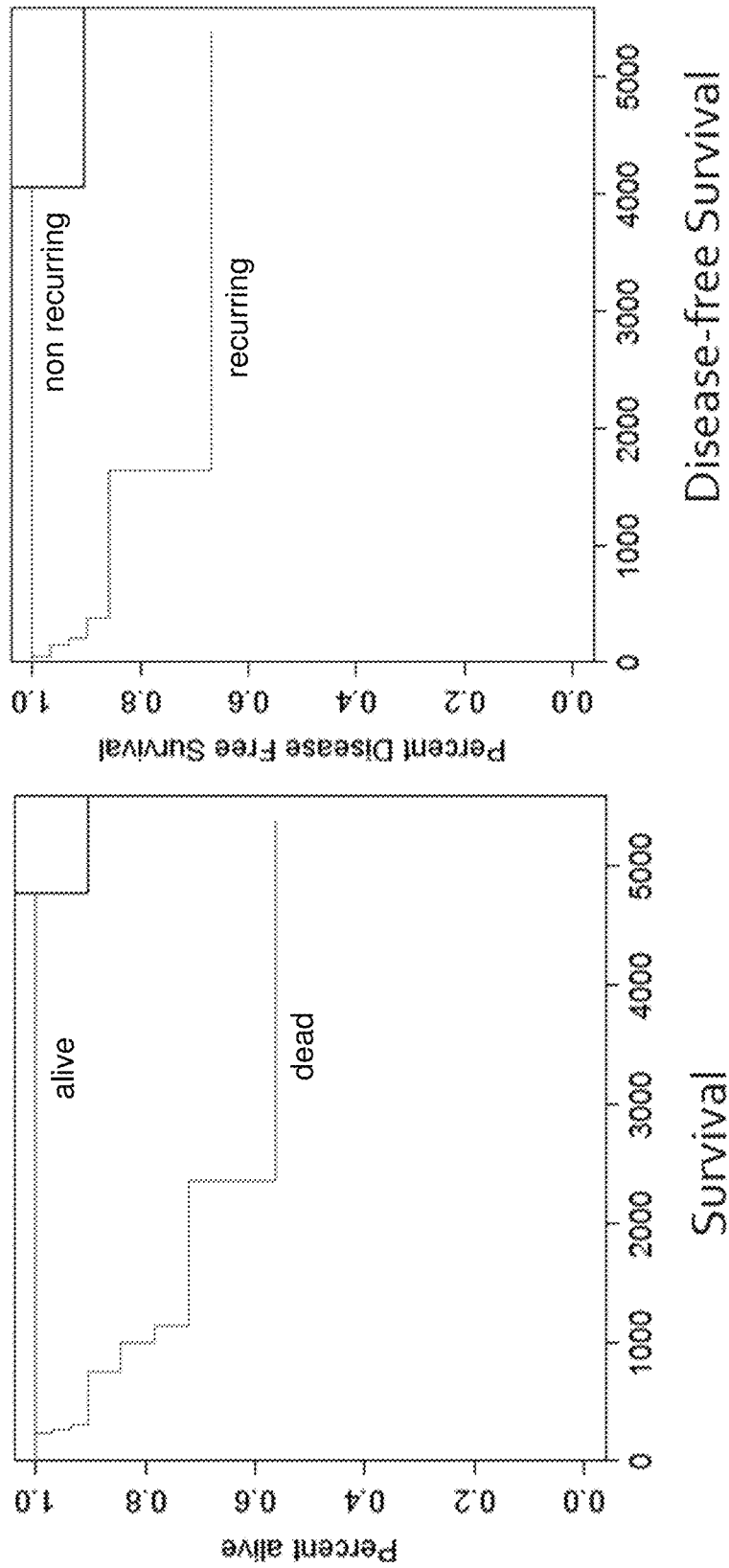
FIG. 6 provides graphs showing survival curves for Multinode Phylogeny WGS Predictions by SVM.

FIG. 5 shows results using Two-Node WES Predictions by SVM. FIG. 6 shows results using Multinode WGS Predictions by SVM. Table 4 provides a summary of data using the SVM algorithm.

TABLE 4

Quantitative Performance of Classifiers (SVM)

| | 2-Node WES Prediction | | | Multinode WGS Prediction | | |
|---|---|---|---|---|---|---|
| | Clinical | Genomic | Both | Clinical | Genomic | Both |
| Accuracy | | | | | | |
| Survival | .694 | 0.758 | 0.620 | 0.780 | 0.829 | 0.829 |
| Recurrence-free Survival | .710 | .694 | .701 | 0.853 | 0.878 | 0.854 |

TABLE 4-continued

Quantitative Performance of Classifiers (SVM)

| | 2-Node WES Prediction | | | Multinode WGS Prediction | | |
|---|---|---|---|---|---|---|
| | Clinical | Genomic | Both | Clinical | Genomic | Both |
| F1 Statistic | | | | | | |
| Survival | .819 | .862 | .761 | .873 | .907 | .907 |
| Recurrence-free Survival | .825 | 0.19 | 0.825 | 0.919 | .935 | 0.921 |

Additional Work

SV discovery and deconvolution—complete work in progress on considering allele-specific SVs for tumor samples with subclones and connect SVs to other functional genomic data such as gene expressions.

Tumor phylogenetics—incorporate more comprehensive variant sets into phylogenetic inference and extracting broader classes of localized, context-specific, and mechanism-specific mutation features.

Machine learning—feature selection to combine clinical, classical genomic, and evolutionary features and methodological innovation on ML to optimize for unbalanced classes.

EXAMPLE 3

The same process as Example 1 was performed using the International Cancer Genome Consortium (ICGC) dataset. Results of the study are provided below in Tables 5 and 6.

In order to validate the effectiveness and generality of this approach, we compiled three sets of data testing various conditions under which the approach might be applied. These datasets cover:

Datasets from two data sources: TCGA and ICGC

Three cancer types: BRCA, subtypes of lung cancer (LUCA): LUAD+LUSC

Two different sequencing strategies: WES, WGS

Four variant callers: TCGA pipeline, Weaver, novoBreak, Sanger pipeline

Two phylogenetic methods: Canopy (SNV+CNA), TUSV (CAN+SV)

Two prognostic prediction tasks: OS, DFS

We selected breast and lung cancers for validation primarily due to their relatively large TCGA and ICGC cohorts. The details of statistics and settings for these datasets are shown below in Table 5, followed by the performance of prognostic prediction in Table 6.

TABLE 5

Statistics of the experiments an datasets in the study.

| Exp | Dataset | Cancer Type | Seq. Strat. | Variant Caller | Phyl. Model | Size | Event/Censored | |
|---|---|---|---|---|---|---|---|---|
| | | | | | | | OS | DFS |
| 1 | TCGA | BRCA | WES | TCGA | Canopy | 1044 | 145/897 | 102/764 |
| | | LUAD | WES | TCGA | Canopy | 516 | 182/325 | 181/268 |
| 2 | TCGA | BRCA | WGS | Weaver | TUSV | 28 | 5/23 | 3/19 |
| | | LUAD | WGS | novoBreak | TUSV | 59 | 29/30 | 25/18 |
| 3 | ICGC | BRCA | WGS | Sanger | TUSV | 90 | 17/73 | 14/59 |
| | | LUCA | WGS | Sanger | TUSV | 89 | 44/43 | 29/38 |

TABLES 6

Performance of prognostic prediction with different features in Exp 2 and Exp 3 WGS sample

|  | Experiment 2 | | | | Experiment 3 | | | |
| --- | --- | --- | --- | --- | --- | --- | --- | --- |
|  | BRCA | | LUAD | | BRCA | | LUCA | |
| Feature | OS | DFS | OS | DFS | OS | DFS | OS | DFS |
| clinical | 80.2 | — | 64.3 | 56.3 | 73.8 | 84.8 | 69.4 | 67.5 |
| driver | 75.3 | — | 33.0 | 31.7 | 66.0 | 76.6 | 60.7 | 55.2 |
| cumulative | 60.5 | — | 55.2 | 59.1 | 54.4 | 56.5 | 57.3 | 57.5 |
| phylogenetic | 61.7 | — | 57.3 | 51.7 | 54.6 | 59.0 | 43.6 | 44.2 |
| clinical + driver | 85.2 | — | 64.8 | 56.5 | 76.8 | 87.7 | 71.3 | 71.7 |
| clinical + cumulative | 80.2 | — | 68.2 | 65.0 | 73.8 | 87.3 | 72.1 | 74.5 |
| clinical + phylogenetic | 80.2 | — | 67.1 | 62.5 | 74.0 | 85.0 | 69.4 | 67.8 |
| clinical + genomic | 85.2 | — | 70.0 | 66.4 | 77.7 | 91.1 | 72.1 | 76.5 |
| clinicalΔ | 55.6 | — | 58.0 | 48.7 | 61.0 | 71.8 | 64.6 | 62.5 |
| clinicalΔ + driver | 71.6 | — | 62.3 | 48.7 | 71.1 | 79.3 | 68.1 | 68.9 |
| clinicalΔ + cumulative | 56.8 | — | 70.1 | 54.3 | 69.1 | 72.5 | 68.1 | 75.0 |
| clinicalΔ + phylogenetic | 69.1 | — | 69.9 | 53.6 | 69.1 | 71.8 | 65.7 | 65.4 |
| clinicalΔ + genomic | 71.6 | — | 71.7 | 57.3 | 71.1 | 81.1 | 68.1 | 76.6 |

Although non-limiting embodiments have been described in detail for the purpose of illustration based on what may be considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

Publications cited herein are incorporated by reference for their technical disclosure to the extent they are consistent with the present disclosure.

We claim:

1. A system comprising at least one processor and a non-transitory computer-readable medium storing program instructions configured to cause the at least one processor to:
    generate sequence variation data that identifies, characterizes, or quantifies at least one mutation in tumor sequence data of a tumor of a patient as compared to normal sequence data obtained from normal cells of the patient or as compared to reference sequence data, wherein the at least one mutation comprises at least one of the following: at least one single nucleotide variation, at least one copy-number alteration, at least one structural variation, or any combination thereof;
    generate, using the sequence variation data, one or more phylogenic trees depicting clonal evolution of cells in the tumor of the patient, each of the generated one or more phylogenic trees comprising a plurality of nodes representing tumor cell clones and edges describing inferred evolutionary relationships between the plurality of nodes;
    determine at least one value quantifying information for the generated one or more phylogenic trees, wherein the determined at least one value is representative of at least one of: a mean, maximum, minimum, or variance in a number of mutations along a path between two leaf nodes of the generated one or more phylogenic trees; a number of mutations from a root node to a leaf node of the generated one or more phylogenic trees; a total number of single-nucleotide variations, copy-number alterations, or structural variations in the generated one or more phylogenic trees; a topological measure of the trees characterizing their evolutionary trajectories; or an overall rate of single nucleotide variations, copy-number alterations, or structural variations for the generated one or more phylogenic trees; and
    train, with a classification algorithm or a regression algorithm, a machine learning model, based on the determined at least one value of the generated one or more phylogenic trees and one or more clinical features of the patient, the one or more clinical features including at least one of cancer status, age at initial diagnosis, and pathologic stage, the machine learning model generating a projection for the patient comprising a clinical outcome or disease progression.

2. The system of claim 1, wherein the tumor sequence data comprises a whole genome sequence or a whole exome sequence of cells of the tumor of the patient.

3. The system of claim 2, wherein the normal sequence data is obtained from normal cells or other source of normal genetic material of the patient and is whole genome sequence data.

4. The system of claim 1, wherein the machine learning model is a classification model configured to produce a measure of patient survival or a measure of cancer metastasis as an output representing the projection for the patient comprising the clinical outcome.

5. The system of claim 1, wherein the machine learning model is a classification model configured to produce a value indicating survival of the patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as an output representing the projection for the patient comprising the clinical outcome.

6. The system of claim 1, wherein the machine learning model comprises a regression model trained to produce a patient survival curve as an output representing the projection for the patient comprising the clinical outcome.

7. The system of claim 1, wherein the determined at least one value quantifies at least one of the overall rate of single nucleotide variations, the overall rate of copy-number alterations, or the overall rate structural variations for the generated one or more phylogenic trees, and
    wherein the at least one processor is configured to train the machine learning module based on the determined at least one value quantifying the overall rate of single nucleotide variations, the overall rate of copy-number alterations, or the overall rate structural variations for the generated one or more phylogenic trees.

8. The system of claim 1, wherein the generated one or more phylogenic trees generated using the sequence variation data comprises a two-node tumor phylogency tree comprising a single ancestral and a single tumor clone.

9. The system of claim 1, wherein the one or more phylogenic trees generated using the sequence variation data comprises a complex phylogeny tree describing multiple related tumor clones.

10. A computer-implemented method comprising:
    receiving or preparing, with at least one processor, a sequence data file comprising tumor sequence data of cells of a tumor of a patient;
    generating, with the at least one processor, sequence variation data that identifies, characterizes, or quantifies at least one mutation in the tumor sequence data as compared to normal sequence data obtained from normal cells of the patient or as compared to reference sequence data, wherein the at least one mutation comprises at least one of the following: at least one single nucleotide variation, at least one copy-number alterations, at least one structural variation, or any combination thereof;
    generating, with the at least one processor, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes;
    determining, with the at least one processor, at least one value quantifying information for the generated one or more phylogenic trees, wherein the determined at least one value is representative of at least one of: a mean, maximum, minimum, or variance in a number of mutations along a path between two leaf nodes of the generated one or more phylogenic trees; a number of mutations from a root node to a leaf node of the generated one or more phylogenic trees;
    a total number of single-nucleotide variations, copy-number alterations, or structural variations in the generated one or more phylogenic trees; a topological measure of the trees characterizing their evolutionary trajectories; or an overall rate of single nucleotide variations, copy-number alterations, or structural variations for the generated one or more phylogenic trees; and
    training, with a classification algorithm or a regression algorithm and with the at least one processor, based on the determined at least one value of the generated one or more phylogenic trees and one or more clinical features of the patient, the one or more clinical features including at least one of cancer status, age at initial diagnosis, and pathologic stage, a machine learning model, the machine learning model generating a projection for the patient comprising a clinical outcome or disease progression for the patient.

11. The computer-implemented method of claim 10, further comprising generating, with the at least one processor, an output representing the projection, the output configured to be used to adapt a treatment process of the patient based on the output.

12. The computer-implemented method of claim 10, wherein the tumor sequence data comprises a whole genome sequence or a whole exome sequence of the cells of the tumor.

13. The computer-implemented method of claim 10, wherein the normal sequence data is obtained from normal cells or other source of normal genetic material of the patient, and wherein the normal sequence data is whole genome sequence data.

14. The computer-implemented method of claim 11, wherein the machine learning model is a classification model trained to produce a measure of patient survival or a measure of cancer metastasis as the output representing the projection of the clinical outcome for the patient.

15. The computer-implemented method of claim 11, wherein the machine learning model is a classification model configured to produce a value indicating survival of the patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as the output representing the projection for the patient comprising the clinical outcome.

16. The computer-implemented method of claim 11, wherein the machine learning model is a regression model trained to produce a patient survival curve as the output representing the projection of the clinical outcome for the patient.

17. A non-transitory computer storage medium storing program instructions configured to cause at least one processor to:
    generate sequence variation data that identifies, characterizes, or quantifies at least one mutation in tumor sequence data of a tumor of a patient as compared to normal sequence data obtained from normal cells of the patient or as compared to reference sequence data, wherein the at least one mutation comprises at least one of the following: at least one single nucleotide variation, at least one copy-number alteration, at least one structural variation, or any combination thereof;
    generate, using the sequence variation data, one or more phylogenic trees depicting clonal evolution of cells in the tumor of the patient, each phylogenic tree comprising a plurality of nodes representing tumor cell clones and edges describing inferred evolutionary relationships between the plurality of nodes;
    determine at least one value quantifying information for the generated one or more phylogenic trees, wherein the determined at least one value is representative of at least one of: a mean, maximum, minimum, or variance in a number of mutations along a path between two leaf nodes of the generated one or more phylogenic trees; a number of mutations from a root node to a leaf node of the generated one or more phylogenic trees; a total number of single-nucleotide variations, copy-number alterations, or structural variations in the generated one or more phylogenic trees; a topological measure of the trees characterizing their evolutionary trajectories; or an overall rate of single nucleotide variations, copy-number alterations, or structural variations for the generated one or more phylogenic trees; and train, with a classification algorithm or a regression algorithm, a machine learning model, based on the determined at least one value of the generated one or more phylogenic trees and one or more clinical features of the patient, the one or more clinical features including at least one of cancer status, age at initial diagnosis, and pathologic stage, the machine learning model generating a projection for the patient comprising a clinical outcome or disease progression.

18. The non-transitory computer storage medium of claim 17, wherein the tumor sequence data comprises a whole genome sequence or a whole exome sequence of cells of a tumor of the patient, and wherein the normal sequence data is obtained from normal cells of the patient and comprises whole genome sequence data.

19. The non-transitory computer storage medium of claim 17, wherein the machine learning model is a classification model trained to produce a value indicating survival of the patient at a predefined future time, risk of death of the patient within a defined time period, metastasis of the tumor at a predefined future time, risk of metastasis of the tumor, risk of the tumor advancing through a defined disease progression state, or stratification of a population of patients into discrete risk levels for a disease progression process, as the output representing the projection for the patient comprising the clinical outcome.

20. The non-transitory computer storage medium of claim 17, wherein the machine learning model comprises a regression model trained to produce a patient survival curve as an output representing the projection of the clinical outcome for the patient.

* * * * *

UNITED STATES PATENT AND TRADEMARK OFFICE
CERTIFICATE OF CORRECTION

| | |
|---|---|
| PATENT NO. | : 12,046,326 B2 |
| APPLICATION NO. | : 16/854378 |
| DATED | : July 23, 2024 |
| INVENTOR(S) | : Russell Schwartz et al. |

It is certified that error appears in the above-identified patent and that said Letters Patent is hereby corrected as shown below:

In the Claims

Column 37, Line 21, Claim 8, delete "phylogency" and insert -- phylogenic --

Signed and Sealed this
Nineteenth Day of November, 2024

Katherine Kelly Vidal
*Director of the United States Patent and Trademark Office*